(12) United States Patent
Xu et al.

(10) Patent No.: US 10,088,348 B2
(45) Date of Patent: Oct. 2, 2018

(54) ULTRASONIC GAS FLOW METER BASED ON FPGA AND DSP

(71) Applicant: HEFEI UNIVERSITY OF TECHNOLOGY, Hefei (CN)

(72) Inventors: Kejun Xu, Hefei (CN); Min Fang, Hefei (CN); Wei Wang, Hefei (CN); Wenjiao Zhu, Hefei (CN); Ziwen Shen, Hefei (CN)

(73) Assignee: HEFEI UNIVERSITY OF TECHNOLOGY, Hefei (CN)

( * ) Notice: Subject to any disclaimer, the term of this patent is extended or adjusted under 35 U.S.C. 154(b) by 0 days.

(21) Appl. No.: 15/688,898

(22) Filed: Aug. 29, 2017

(65) Prior Publication Data

US 2018/0010943 A1     Jan. 11, 2018

Related U.S. Application Data

(63) Continuation of application No. PCT/CN2016/077122, filed on Mar. 23, 2016.

(30) Foreign Application Priority Data

Mar. 24, 2015    (CN) .......................... 2015 1 0130389

(51) Int. Cl.
     *G01P 3/00*        (2006.01)
     *G01F 1/66*        (2006.01)
     *G01F 1/74*        (2006.01)
     *G01N 29/032*    (2006.01)

(52) U.S. Cl.
     CPC .............. *G01F 1/667* (2013.01); *G01F 1/662* (2013.01); *G01F 1/74* (2013.01); *G01N 29/032* (2013.01)

(58) Field of Classification Search
     CPC ............ G01F 1/66; G01F 1/74; G01N 29/032
     See application file for complete search history.

(56) References Cited

U.S. PATENT DOCUMENTS

| | | | | |
|---|---|---|---|---|
| 8,249,829 | B2 * | 8/2012 | Vass | G05B 19/41865 340/635 |
| 9,414,183 | B2 * | 8/2016 | Wang | H04W 4/02 |
| 9,824,503 | B2 * | 11/2017 | Yu | G06T 19/20 |

* cited by examiner

*Primary Examiner* — Jewel V Dowtin
(74) *Attorney, Agent, or Firm* — Hemisphere Law, PLLC; Zhigang Ma

(57) ABSTRACT

An ultrasonic gas flow meter based on FPGA and DSP consists of ultrasonic gas transducers and sensor components, transmitting/receiving signal channel switch circuits, a driving signal generation and amplification circuit, an echo signal conditioning and collection circuit, a time sequential controlling and signal processing circuit, a man-machine interface, a serial communication module and a power management module, propagation time of ultrasonic echo waves is calculated by adopting a variable ratio threshold and zero-crossing detection method of tracking maximum peak of the echo signal to obtain gas flow rates.

11 Claims, 15 Drawing Sheets

ULTRASONIC GAS FLOW METER BASED ON FPGA AND DSP

TECHNICAL FIELD

The disclosure relates to a flow measurement field, which is an ultrasonic gas flow meter, and more particularly to an ultrasonic gas flow meter based on a dual-core structure consisting of a FPGA (field-programmable gate array) chip and a DSP (digital signal processor) chip. The ultrasonic gas flow meter aims at an ultrasonic echo signal generated by sine wave excitation, adopts a variable ratio threshold method of tracking a maximum peak of an echo signal, and is simultaneously combined with a zero-crossing detection method.

DESCRIPTION OF RELATED ART

An ultrasonic gas flow meter has unique superiority in measuring accuracy, reliability, pressure loss, maintenance fees, manufacture costs and other aspects compared with other gas flow meters (i.e. an orifice plate, a turbine flow meter, etc.), especially in measuring flow rates of pipes with middle and large calibers, the advantages will be more apparent. The transit time based ultrasonic gas flow meter is the most widely applied among them. The ultrasonic gas flow meter is formed by two sections, one is the transducer and sensor section, including one or more pairs of ultrasonic transducers, pressure sensors and temperature transducers. The other is a transmitter, including a part generating and adjusting driving signals, a part adjusting echo signals and processing data, and a human-machine interaction part. A key to develop the ultrasonic gas flow meter is selecting proper ultrasonic driving signals, simultaneously preventing influence of noisy signals mixed in the echo signals, then propagation time of a downstream ultrasonic wave and an upstream ultrasonic wave can be achieved respectively based on a stable feature point of the echo signals.

For clear description, signals loaded on a transmitting ultrasonic transducer are defined as driving signals, the transmitting ultrasonic transducer emits ultrasonic waves. A receiving ultrasonic transducer receives ultrasonic waves, signals output from the receiving ultrasonic transducer are echo signals. The ultrasonic transducer can be applied to emit and receive, the transmitting/receiving signal channel switch circuits control the switch of functions thereof.

Other countries first applied digital signal processing technology in the ultrasonic gas flow meter, methods are summarized as follows.

(1) A Method Based on Energy Mutation

US Company Daniel adopted a method of searching for a feature point by detecting energy mutation (William Freund, Winsor Letton, James Mc-Clellan, Baocang Jia, Anni Wey, Wen Chang. Method and apparatus for measuring the time of flight of a signal, U.S. Pat. No. 5,983,730, Nov. 16, 1999). As energy of the echo signals undergoes a process from weak to strong and a process from strong to weak, an energy variance ratio of the echo signals first increases then decreases, propagation time of the ultrasonic waves can be achieved by a critical point of the energy variation ratio. Specifically, the method firstly achieves squares of amplitudes of each point of the echo signals, values of the squares of the amplitudes represent values of signal energy. Subsequently, average energy of each of the points is achieved by a method of moving average, then a variation curve of an average energy ratio of a former point and a latter point is drew, which is an energy variation ratio curve. Finally, the propagation time of the ultrasonic waves is achieved by the critical point of the energy variation ratio. However, the patent conceals crucial parameters of the process, such as timespan of moving window, timespan between the former point and the latter point during achieving the energy variation ratio, etc.

(2) A Method Based on Phase Mutation

Austria AVL List GmbH (Mario Kupnik, Andreas Schroder, Michael Wiesinger, Klaus-Christoph Harms. Ultrasonic gas flow meter as well as device to measure exhaust flows of internal combustion engines and method to determine flow rate of gases, US Patent NO. 2005/0066744A1, Mar. 31, 2005) monitors the phase mutation of the ultrasonic echo signal to achieve flow measurement. A point with maximum amplitude of the echo signal is firstly observed, and phase information of the signal is obtained by calculation of Hilbert transform, taking the moment corresponding to the point with the maximum amplitude of the echo signal as the origin, a time is determined in the direction of the transmission time at which the continuous change of the phase position comes to a halt. A first zero-crossing point of the echo signal is determined by the phase mutation point, further obtaining ultrasonic propagation time. However, the method needs a great amount of calculation, and easily affected by noise, which can hardly be a choice in practical industries.

(3) A Method Based on Addition of Multiple Time-Shifted Copies

In order to enhance a signal-to-noise ratio of an echo signal, Dutch company Instromet adopted a method of addition of multiple time-shifted copies (Eduard Johannes Botter. Ultrasonic signal processing method and applications thereof, U.S. Pat. No. 725,449,462, Aug. 7, 2007). The method firstly sends 8 driving signals with predefined timespan successively, corresponding 8 echo signals are obtained, subsequently, the 8 echo signals are shifted and added according to predefined time to strength the echo signals, while the noisy signals will be declined due to mutual counteraction in the addition process caused by randomness thereof. Finally, the propagation time of ultrasonic waves is achieved by a method of threshold detection. The method utilizes respective time domain feature of the echo signals and noisy signals to enhance the signal-to-noise ratio efficiently. However, repeated emission of the ultrasonic driving signals can extend measuring time of the system and affects dynamic response of the flow meter. When flow mutates, apparent errors in measurement will appear.

(4) A Method Based on Cross-Correlation and Derivative thereof

In operation of the ultrasonic flow meter, the downstream echo signal and the upstream echo signal are related, but the noisy signals have no correlation, so that a transit time difference of ultrasonic waves can be calculated by the method of cross-correlation and derivative thereof. A conventional cross-correlation calculation is shown as equation (1), a downstream echo signal is supposed to be x(t), an upstream echo signal is supposed to be y(t), time displacement $\tau$ corresponding to $R_{xy}(\tau)$ taking the maximum value is the difference of propagation time in downstream propagation and in upstream propagation. The conventional cross-correlation method needs a great amount of calculation, which can hardly be achieved by limited resources of a microcontroller. In order to reduce calculation of cross-correlation, Tokyo keiso Co., Ltd. in Japan adopted a cross-correlation derivative algorithm (Tokio Sugl, Tadao Sasaki. Ultrasonic flow meter, U.S. Pat. No. 007,299,150B1, Nov. 20, 2007), shown as equation (2), m is shift amount, N is sample value, the shift amount m at which the cross-correlation $S_{xy}(m)$ becomes maximum denotes a transit time difference between the downstream and upstream propagating ultrasonic waves. It can be found by comparing equations (1) and (2) that the cross-correlation derivative calculation substitutes addition and modulo operation for multiplication in the original cross-correlation calculation to reduce the amount of calculation. However, errors of measurement come along as well, especially in noisy environment, calculation mistakes are highly possible coming out.

$$R_{xy}(\tau) = \lim_{T\to\infty} \frac{1}{T} \int_0^T x(t)y(t+\tau)dt \quad (1)$$

$$S_{xy}(m) = \sum_{n=1}^{N} |x(n) - y(n+m)| \quad (2)$$

(5) A Method Based on Combination of Cross-Correlation and Zero-Crossing Detection Siemens AG of Germany adopted a method of combining zero-crossing detection and cross-correlation to calculate absolute downstream and upstream propagation time of ultrasonic waves (Arthur Freund, Nils Kroemer. Method for measuring the time of flight of electric, electromagnetic or acoustic signals, EP Patent NO. 0797105A2, Mar. 17, 1997), firstly an echo signal without noise is obtained by some method, initiative time thereof is supposed to be $t_0$, one zero-crossing point is selected in the echo signal simultaneously, the time interval of the zero-crossing point and the initiative time $t_0$ denotes $t_N$. Subsequently, the echo signal and an echo signal adopted by a transducer practically are cross-correlated. If the time interval of the maximum value of the cross-correlation result is $t_d$, and the time interval of initiative time of the practical echo signal and emission time of the driving signal is supposed to be $t_1$, then the propagation time of the echo signal is:

$$t = t_1 + t_d + t_N - t_{korr} \quad (3)$$

where $t_{korr}$ is adjusting time, it includes transducer transforming delay and circuit transmission delay. The method can detect echo signals in received waveforms with noisy signals reliably, as the zero-crossing point has relative high amplitude resolution around, which is fit for noisy worksite. However, the patent did not disclose how to obtain the echo signal without noise, in addition, problems such as including a great amount of cross-correlation calculation exist as well.

SUMMARY

In order to improve calculation accuracy of the propagation time and interference prevention of the system, the disclosure provides an ultrasonic gas flow mete based on FPGA and DSP.

An ultrasonic gas flow meter transmitter based on FPGA and DSP consists of ultrasonic gas transducers and sensor components, transmitting/receiving signal channel switch circuits, a driving signal generation and amplification circuit, an echo signal conditioning and collection circuit, a time sequential controlling and signal processing circuit, a man-machine interface, a serial communication module and a power management module. The ultrasonic gas transducers and sensor components consists of four transducers, a pressure sensor and a temperature sensor. The four transducers, the pressure sensor and the temperature sensor are fixed on the gas pipeline, respectively. Each of the transducers acts as a transmitting transducer as well as a transmitting transducer. The transmitting/receiving signal channel switch circuits consist of excitation strobe circuits, transformer amplification circuits and four echo strobe circuits. The four echo strobe circuits have the same structure, and connected with the transducers, respectively. The driving signal generation and amplification circuit consists of a high speed DAC (digital to analog converter) signal generation and output circuit, a driving signal voltage and power amplification circuit. The echo signal conditioning and collection circuit consists of a voltage amplification circuit, a bandpass filter circuit, an automatic gain control circuit, a single-ended-to-differential conversion circuit, a biasing circuit, and a high speed ADC (analog to digital converter) signal collection and conversion circuit. The time sequential controlling and signal processing circuit consists of a FPGA circuit system and a DSP circuit system, the FPGA circuit system mainly consists of a FPGA chip, a FPGA chip serial configurator circuit, and a FPGA chip reset and configuration button circuit. The DSP circuit mainly consists of a DSP chip and a DSP chip booting mode selection circuit. The FPGA chip is used to temporarily store the conversion code value sent by the echo signal conditioning and collection circuit, the conversion code value will be transmitted to the DSP chip when delayed time is reached. The DSP chip is a master control chip, responsible for processing digital signals, human-computer Interaction and serial communication, as well as the cooperation with the FPGA circuit system to control sequence of the entire system. The DSP chip adopts digital filtering to eliminate noise in signals, and a variable ratio threshold and zero-crossing detection method of tracking maximum peak of the echo signal is adopted to calculate the propagation time of an ultrasonic echo, so as to obtain the gas flow rates.

A method to control an ultrasonic gas flow meter transmitter based on FPGA and DSP is achieved by a main monitoring program and various subroutine modules. The main monitoring program is a master scheduling program, the various subroutine modules are an initialization module, a transmitting/receiving signal channel switch module, a data transmission to FPGA module, an interrupt service routine, a calculation module, a FRAM (ferromagnetic random access memory) read-write module, a serial interface communication module, a pulse output module, a keyboard input module, and a liquid crystal display module. The main monitoring program implements each function of the ultrasonic gas flow meter transmitter by calling each subroutine module.

Specific manipulation steps of the main monitoring program are as follows.

(1) Initialization of the Circuit System

After the circuit system is powered, the DSP chip accomplishes initialization of each section: including assigning GPIO (general purpose input output) ports of the DSP chip, interrupt initialization of an internal timer 1 of the DSP chip, initializing a liquid crystal display module, reading accumulated flow rates in the FRAM read-write module, initializing each parameter of a meter, and creating 4 queues, each of the queues consists of 50 digital vacancies. The 4 queues are configured to store the propagation time of ultrasonic waves received by 4 transducers (short for propagation time in the following). Whenever one new propagation time data enters, data on the front of each of the queues will be abandoned, the new propagation time data will be added on the end of the queue. In a subsequent measuring process, average downstream and upstream propagation times of dual channel ultrasonic gas flow meter will be calculated in real time according to data of the 4 queues.

(2) Circulation of Flow Measurement

The program enters circulation of flow measurement after the circuit system is initiated. Firstly the DSP chip switches transmitting and receiving channels of transducers by changing output status of corresponding GPIO ports. Order of switching channels is: the first transducer 1 transmits while the third transducer 3 receives, the second transducer 2 transmits while the fourth transducer 4 receives, the third transducer 3 transmits while the first transducer 1 receives, and the fourth transducer 4 transmits while the second transducer 2 receives. Switching processes above are cycled continuously. The FPGA chip is noticed to measure after switching channels, the DSP chip needs to wait for the FPGA chip to receive signals.

(3) Waiting for the FPGA Chip to Control the High Speed DAC and the High Speed ADC to accomplish the Signal Drive and Echo Signal Collection.

The DSP chip sends a start-to-measure signal to the FPGA chip, the FPGA chip immediately enables an internal delayed module, and waveform data stored in a ROM (read-only memory) module in the FPGA chip is called simultaneously to be transferred to the driving signal generation and amplification circuit, then output to the first transducer 1, or the second transducer 2, or the third transducer 3, or the fourth transducer 4 of a direct injection dual channel structure through the transmitting/receiving signal channel switch circuits controlled by the DSP chip, the first transducer 1, or the second transducer 2, or the third transducer 3, or the fourth transducer 4 emits ultrasonic waves. The ultrasonic waves arrive at a corresponding receiving transducer after some propagation time. The third transducer 3, or the fourth transducer 4, or the first transducer 1, or the second transducer 2 receives the ultrasonic waves to form an echo signal. The transmitting/receiving signal channel switch circuits controlled by the DSP chip receive the echo signal emitted from the transducers and input the echo signal to the echo signal conditioning and collection circuit. The high speed ADC in the echo signal conditioning and collection circuit accomplishes data conversion. RAM_2PORT (dual-port random-access memory) module in the FPGA chip is configured to temporarily store the conversion code value of the high speed ADC, when predefined time determined by a delayed circuit is up, the preset GPIO port of the DSP chip is pulled up to notify the DSP chip completion of signal collection.

(4) Data Duplication

The DSP chip duplicates the data stored in the RAM_2PORT module in the FPGA chip to the RAM in the DSP chip after detecting a high level of a preset terminal, so as to provide the DSP chip for processing digital signals.

(5) The DSP Chip Processing the Data, Calculating Propagation Time of the Ultrasonic Waves The DSP chip processes the duplicated data, the propagation time T of each of the ultrasonic waves is calculated to be $$T = 1/8 \sum_{i=1}^{8} \tau_i - t' \qquad (4)$$

where $\tau_i$ (i=1, 2, 3 ... 8) is zero-crossing time, and t' is a stationary deviation value. The deviation value is obtained by calculating at the zero flow rate.

(6) Calculating an Instantaneous Flow Rate

One propagation time of the ultrasonic waves from a transducer to another transducer is obtained by one circulation of steps (2)~(5).

Different transmitting transducers and receiving transducers are switched in step (2) to measure the propagation time of each downstream and upstream propagating channel successively in sequence. After four loops as such measurement of downstream and upstream propagation times of dual channel is accomplished, the four propagation time is placed in the 4 queues created in step (1) respectively.

5 times of such measurement are performed to calculate the average downstream and upstream propagation times of dual channels, an average flow rate is calculated as an instantaneous flow rate to be displayed according to the average propagation time.

An equation of the instantaneous flow rate is:

$$Q = \frac{\pi D^2}{4} \frac{L}{2\cos\theta} \frac{\Delta t}{t_s t_n} = k_f \frac{\Delta t}{t_s t_n} \qquad (5)$$

where Q is an instantaneous flow rate, D is a diameter of a pipe, L is a length of the channel, and θ is an angle of a channel angle. The channel angle is an angle between a propagation path of ultrasonic waves and a pipe axis. $t_s$, $t_n$ and Δt are downstream propagation time, upstream propagation time and the time difference of them, respectively; $k_f$ is a meter parameter. A corrected instantaneous flow rate is obtained after correcting process.

(7) Calculating Accumulated Flow Rate

An interrupt service program for the internal timer 1 of the DSP chip calculates the accumulated flow rate after achieving the corrected instantaneous flow rate to ensure accumulation once one second, which means the timer interrupt is generated by the DSP chip internal timer 1, one period is 1 second. A timer interrupt service routine firstly reads a result of the instantaneous flow rate calculated by the main monitoring program and accumulates to achieve the accumulated flow rate. A parameter of the pulse output module is updated according to a value of the instantaneous flow rate, and the pulse with certain frequency is output to represent the measured instantaneous flow rate. Subsequently, a time marker of the timer is set to be 1 to update the liquid crystal display in the main monitoring program and perform host computer communication.

Beneficial effects of the disclosure are achieving high frequency output of driving signals and high speed sampling of echo signals, as well as processing digital signals in real time based on dual cores—a FPGA chip and a DSP chip, which enhances the calculation accuracy of propagation time and interference prevention of the system, coinciding with requirements in industry applications.

BRIEF DESCRIPTION OF THE DRAWINGS

FIG. 12 is a schematic diagram of a FPGA chip (EP2C8Q208C8N) sub-module—I/O interface.

FIG. 13 is a schematic diagram of a FPGA chip (EP2C8Q208C8N) sub-module—I/O voltage and reference voltage.

DETAILED DESCRIPTION OF PREFERRED EMBODIMENTS

Figure 1:
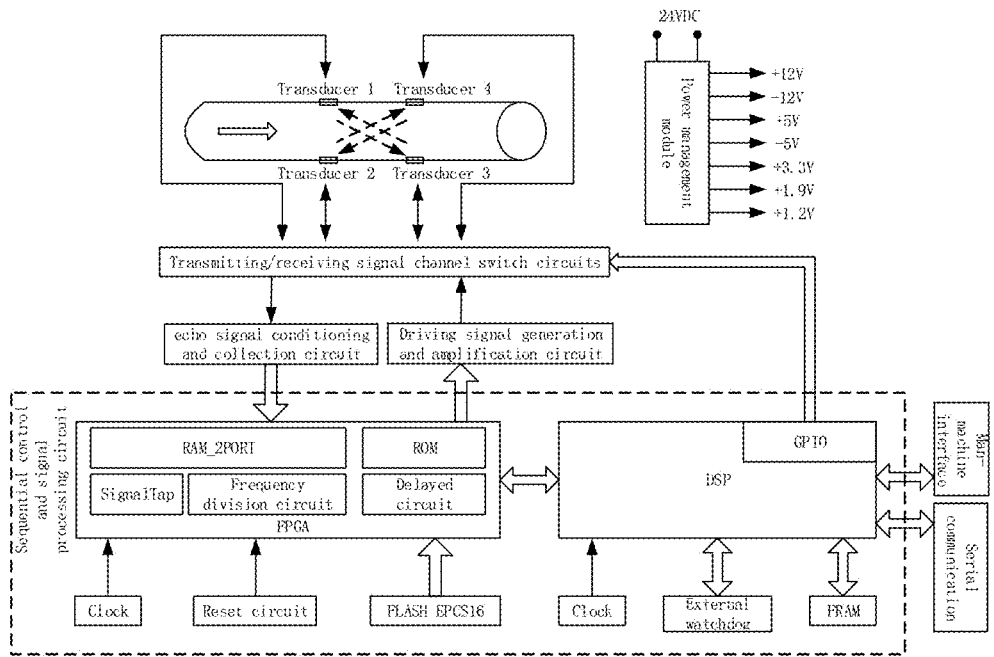
FIG. 1 is a block diagram of system hardware.

Referring to FIG. 1, a hardware system of the disclosure consists of ultrasonic gas transducers and sensor components, transmitting/receiving signal channel switch circuits, a driving signal generation and amplification circuit, an echo signal conditioning and collection circuit, a time sequential controlling and signal processing circuit, a man-machine interface, a serial communication module and a power management module.

The ultrasonic gas transducers and sensor components consists of four transducers, a pressure sensor and a temperature sensor, the four transducers, the pressure sensor and the temperature sensor are fixed on the gas pipeline, respectively. The four transducers are the first transducer 1, the second transducer 2, the third transducer 3 and the fourth transducer 4, which are formed to be a direct injection dual channel structure. Each of the transducers acts as a transmitting transducer as well as a transmitting transducer.

The transmitting/receiving signal channel switch circuits consist of excitation strobe circuits, transformer amplification circuits and four echo strobe circuits.

The driving signal generation and amplification circuit consists of a high speed DAC signal generation and output circuit, a driving signal voltage and power amplification circuit.

The echo signal conditioning and collection circuit consists of a voltage amplification circuit, a bandpass filter circuit, an automatic gain control circuit, a single-ended-to-differential conversion circuit, a biasing circuit, and a high speed ADC signal collection and conversion circuit.

The time sequential controlling and signal processing circuit consists of a FPGA circuit system and a DSP circuit system. The FPGA circuit system mainly consists of a FPGA chip, a FPGA chip serial configurator circuit, and a FPGA chip reset and configuration button circuit, a model of the FPGA chip is EP2C8Q208C8N. The DSP circuit mainly consists of a DSP chip and a DSP chip booting mode selection circuit, a model of the DSP chip is TMS320F28335.

The circuit system of the disclosure is categorized as an analog circuit board and a digital circuit board according to function, the analog circuit board includes the transmitting/receiving signal channel switch circuits, the driving signal voltage and power amplification circuit, the voltage amplification circuit, the bandpass filter circuit, the automatic gain control circuit, the single-ended-to-differential conversion circuit, the biasing circuit, and an analogue power supply (+12V, −12V, +5V, −5V) conversion circuit in a power supply management module. The digital circuit board includes the high speed DAC signal generation and output circuit, the high speed ADC signal collection and conversion circuit, the FPGA circuit system, the DSP circuit system, and a digital power supply (+3.3V, +1.9V, +1.2V) conversion circuit in the power supply management module.

An operational process of the circuit system of the disclosure is that the FPGA chip immediately enables an internal delayed module as soon as receiving a start-to-measure signal from the DSP chip, simultaneously calling waveform data stored in an internal ROM module to be transferred to the driving signal generation and amplification circuit at the speed of 20 MSPS. Driving signals generated by the high speed DAC are output to the transmitting transducer through the transmitting signal channel switch circuit controlled by the DSP chip after voltage and power amplification. The transmitting transducer emits the ultrasonic waves based on the electrostriction effect of piezoelectric crystal. The ultrasonic waves arrive at the corresponding receiving transducer after some propagation time. As the piezoelectric effect of the piezoelectric crystal, the receiving transducer outputs the echo electric signal. The echo electric signal is input to the echo signal conditioning and collection circuit through the receiving signal channel switch circuit controlled by the DSP chip. After amplification, bandpass filtering and automatic gain circuit, the high speed ADC completes data conversion according to the 5 MHz sampling frequency provided by the FPGA chip. A dual-port in the FPGA chip is configured to temporarily store the conversion code values of the high speed ADC. When predefined time determined by a delayed circuit is up, the conversion code values are transferred to the DSP chip through a parallel line. The DSP chip adopts digital filtering to further eliminate noise in the echo signals. The propagation time of ultrasonic echo waves is calculated by the variable ratio threshold and zero-crossing detection method of tracking maximum peak of the echo signal. The first transducer 1, the second transducer 2, the third transducer 3 and the fourth transducer 4 act as a transmitting transducer in sequence, the process above is repeated, real flow rates can be measured by summarizing propagation time of echoes of 4 channels. The transmitter can display through the liquid crystal on-site as well as reading remotely through the serial communication module after the gas flow rates are calculated in the operational mode.

Figure 2:
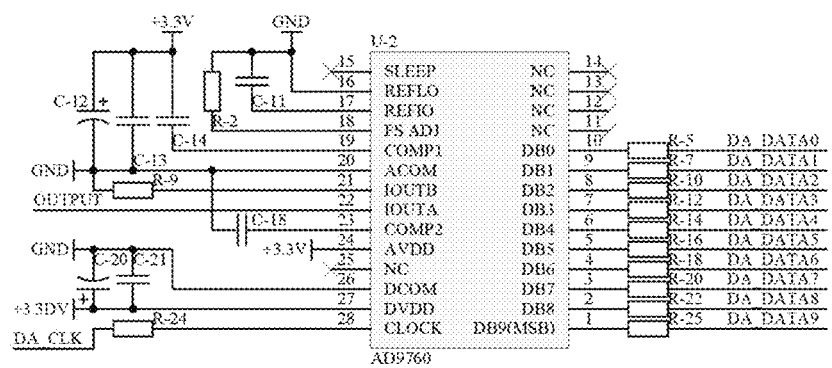
FIG. 2 is a schematic diagram of a high speed DAC signal generation and output circuit.

FIG. 2 is a high speed DAC signal generation and output circuit, consisting of a dual differential line driver U-2, resistors R-2, R-9, R-5, R-7, R-10, R-12, R-14, R-16, R-18, R-20, R-22, R-24, R-25, capacitors C-11, C-12, C-13, C-14, C-18, C-20 and C-21. U-2 is a high speed output DAC, pins DB0 to DB9 of U-2 are connected to corresponding data output pins of FPGA by the resistors R-5, R-7, R-10, R-12, R-14, R-16, R-18, R-20, R-22 and R-25, low-resistance resistors series connected in the data transportation line can be benefit for curbing reflection and vibration of high speed signals. The resistor R-2 is connected to a pin FS ADJ of U-2 to adjust full scale output current values. The capacitors C-11, C-12 and C-13 are decoupling capacitors. The resistor R-9 pulls down output of IOUTB of U-2 to the ground. The capacitors C-14 and C-18 are compensation capacitors, respectively connecting a bandwidth/noise inhibition node COMP1 of U-2 and an internal biasing node COMP2 of the switch driving circuit to power rail 3.3V and the ground. C-20 and C-21 are decoupling capacitors. CLOCK pin of U-2 is connected to a clock output pin of FPGA by the resistor R-24. Conversion results OUTPUT of the high speed DAC is output through the IOUTA pin.

Figure 3:
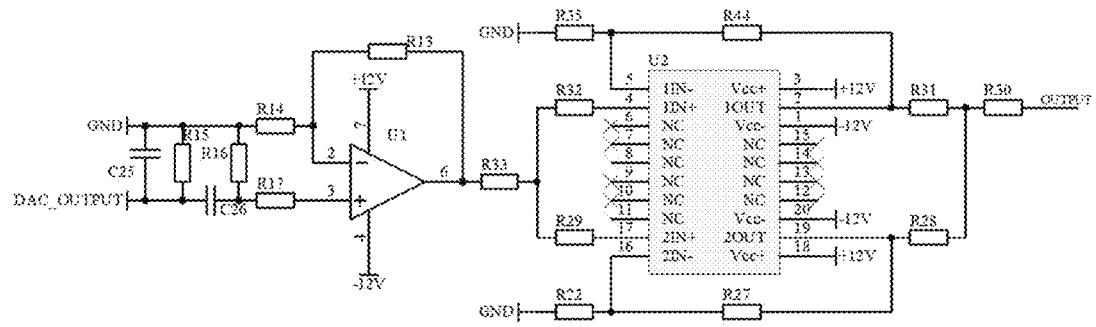
FIG. 3 is a schematic diagram of a driving signal voltage and power amplification circuit.

FIG. 3 is a driving signal voltage and power amplification circuit, consisting of a low noise high speed operational amplifier U1, resistors R13, R14, R15, R16, R17, R22, R27, R28, R29, R30, R31, R32, R33, R35, R44, capacitors C25 and C26. DAC_OUTPUT is a current signal output from the high speed DAC, converted to be a voltage signal by the resistor R16. The capacitor C25 is a filter capacitor, the capacitor C26 is a DC (direct current) blocking capacitor, and the resistor 16 provides a DC path to an in-phase input terminal of U1 to prevent output saturation of the operational amplifier caused by biasing current. The resistor R17 is a matching resistor, which is configured to balance input impedance of the operational amplifier U1. The resistors R13 and R14 are configured to set up voltage gain. U2 is a dual differential line driver, adopting a form of current negative feedback, having features of wide bandwidth, high driving current and low distortion. The resistor R33 acts as connection, the resistors R35, R44, R22 and R27 are configured to set up amplification gain. Two-path output of U2 achieves current in parallel through the resistors R31 and R28 to further inforce power amplification. The driving signals after voltage and power amplification finally are output towards a next level through the resistor R30.

Figure 4:
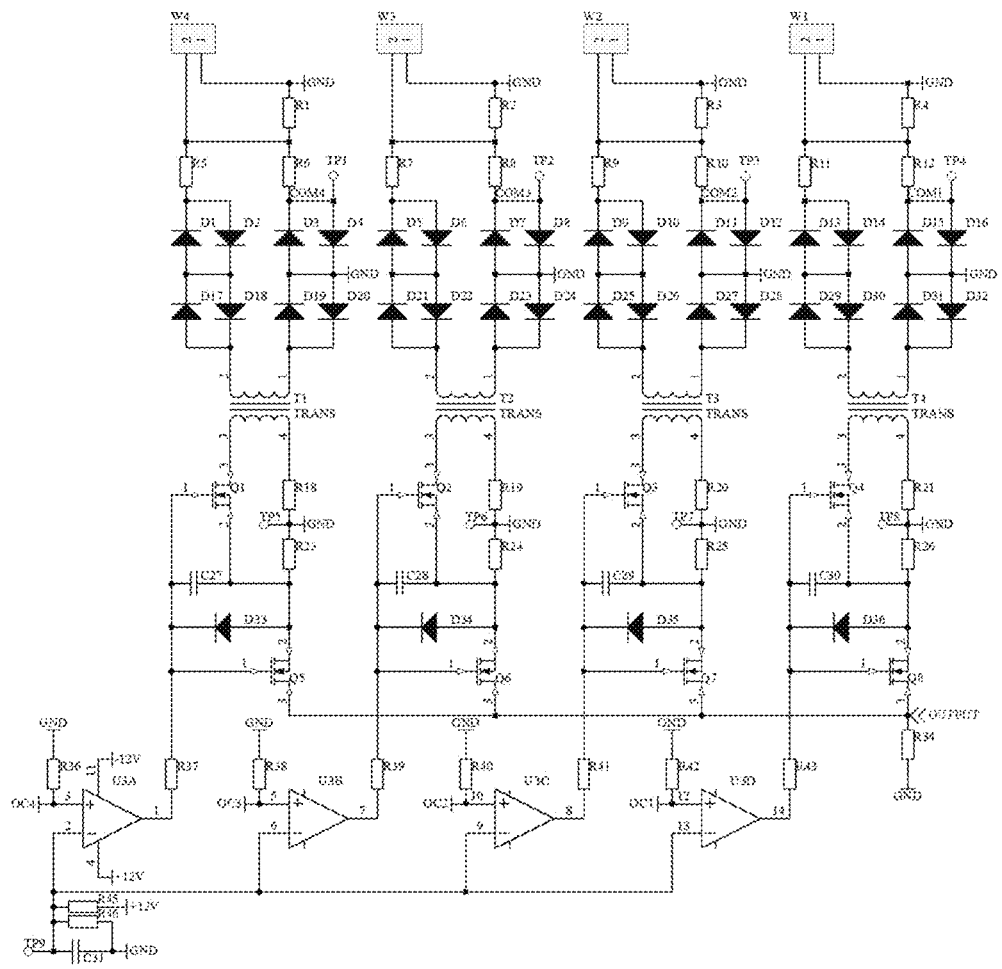
FIG. 4 is a schematic diagram of excitation strobe circuits and transformer amplification circuits.

FIG. 4 is the excitation strobe circuits and transformer amplification circuits. The excitation strobe circuits include four bipolar operational amplifiers U3A, U3B, U3C and U3D. Transformers T1, T2, T3 and T4 form the transformer amplification circuits. T1, T2, T3 and T4 are transformers with turn ratios of 1:10, pins 1, 2 are secondary sides of the corresponding transformer. Pins 3, 4 are primary sides of the corresponding transformer. OUTPUT is the driving signal whose voltage and power are amplified in the pre-stage circuit. OC1, OC2, OC3 and OC4 are transducer transmitting strobe signal output by the DSP. For the sake of convenience, the operational principle of the circuit will be illustrated with OC1 controlling logic as an example firstly, and other channels are similar. When OC1 is set to be low, output voltage of U3D approaches the negative power rail thereof (about −12V), N-groove enhanced mode MOS tubes Q4 and Q8 are turned off, the driving signals cannot arrive at the transducers. When OC1 is set to be high, the output voltage of U3D approaches the positive power rail thereof (about +12V). At the moment, Q4 and Q8 are turned on, and the driving signals arrive at the primary sides of the transformer. The driving signals are amplified by the transformer and finally reach a connecting terminal W1 of the transducer through a rectifying circuit built by several diodes. The resistor R34 is a pull-down resistor, which provides an initial input electrical level to the circuit. The resistors R21 and R26 are pull-down current-limiting resistors. The capacitor C30 and a diode D36 together form a MOS (mosfet) tube Q4 and Q8 guard circuit to prevent accidental breakdown. The resistors R4 and R12 form a voltage division circuit, which can be adjusted according to various features of transducers. The resistor 11 acts as connection. TP4 is a test port. The corresponding COM1 is connected to a transducer of W1 as an echo signal generated in receiving the transducer.

Figure 5:
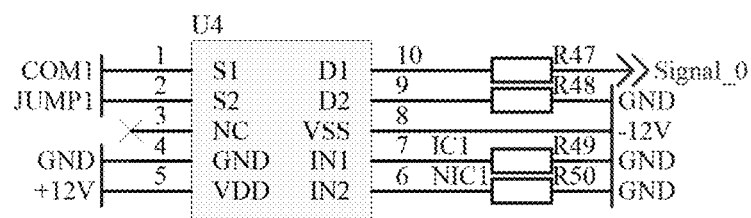
FIG. 5 is a schematic diagram of an echo strobe circuit.

FIG. 5 shows an echo strobe circuit of channel 1, other 3 channels are similar to it. U4 is a dual low impedance single-pole single-throw switch, compatible with 3V logic level, crosstalk in channels is merely −70 dB with power supply of 12V. IC1 and NIC1 are a strobe signal and a cut-off signal of the transducer 1 output from DSP. When IC1 is set to be high, S1 and D1 are gated, which means connecting COM1 to the subsequent echo signal conditioning and collection circuit. JUMP1 is a testing terminal. The resistors R48, R49 and R50 are pull-down resistors. The gated echo signals are output to subsequent circuits through the resistor R47.

Figure 6:
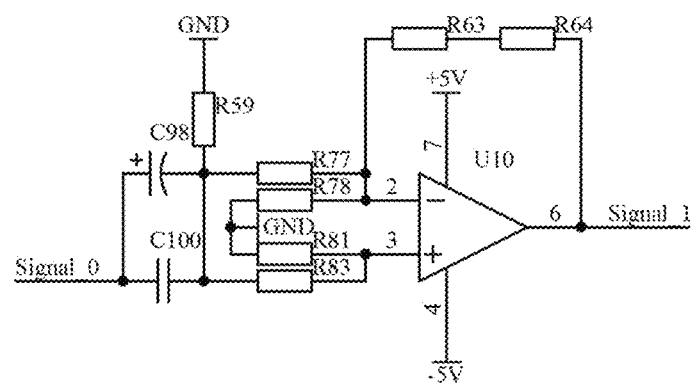
FIG. 6 is a schematic diagram of a voltage amplification circuit.

FIG. 6 is a voltage amplification circuit in the echo signal conditioning and collection circuit, consisting of a low noise high speed operational amplifier U10, capacitors C98, C100, resistors R59, R63, R64, R77, R81, R78 and R83, the resistors R77, R81 and the low noise high speed operational amplifier U10 form an anti-phase amplification circuit. The resistors R78, R83 and the low noise high speed operational amplifier U10 form an in-phase amplification circuit. Signal_0 is an echo signal gated in front, U10 is a low noise high speed operational amplifier. The capacitors C98 and C100 are DC blocking capacitors, the capacitors C98, C100 and the resistor R59 together form a high pass filter. When the resistors R77 and R81 are soldered, the resistors R78 and R83 are ignored, the resistors R77, R81 and a feedback resistor of a post-stage operational amplifier form an anti-phase amplification circuit. When the resistors R78 and R83 are soldered, the resistors R77 and R81 are ignored, the resistors R78, R83 and the feedback resistor of the post-stage operational amplifier form an in-phase amplification circuit, the actual connection way of the two resistors above needs to be selected according to the echo signal feature.

Figure 7:
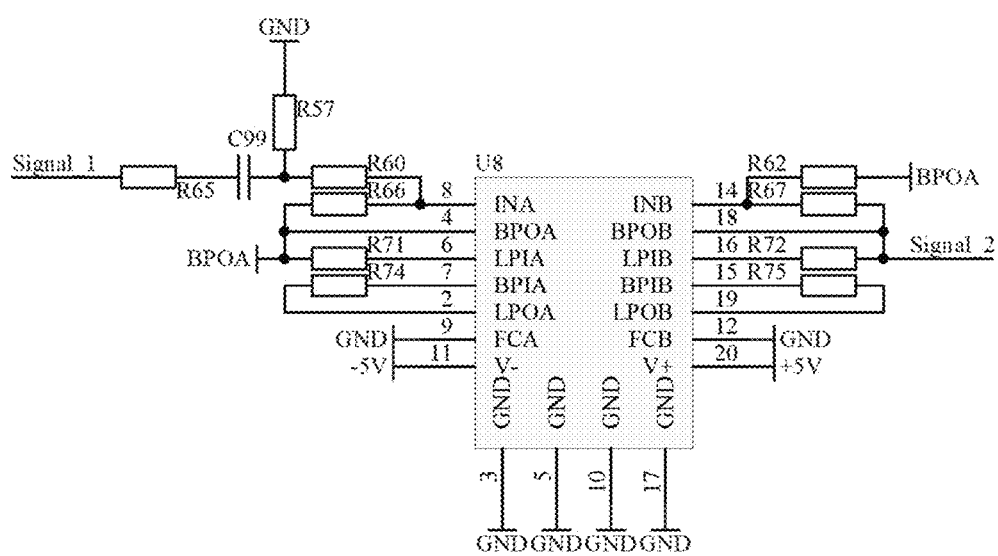
FIG. 7 is a schematic diagram of a bandpass filter circuit.

FIG. 7 shows a bandpass filter circuit in the echo signal conditioning and collection circuit, consisting of a 4-order continuous time active power filter U8, resistors R60, R62, R66, R67, R71, R72, R74 and R75. A center frequency, a bandwidth, a quality factor and a gain parameter of the filter can be changed by adjusting peripheral resistors R60, R66, R71, R74, R62, R67, R72 and R75. The resistor R65 leads the echo signal after front-end conditioning to the filter, the resistor R57 and the capacitor C99 form a high pass filter.

Figure 8:
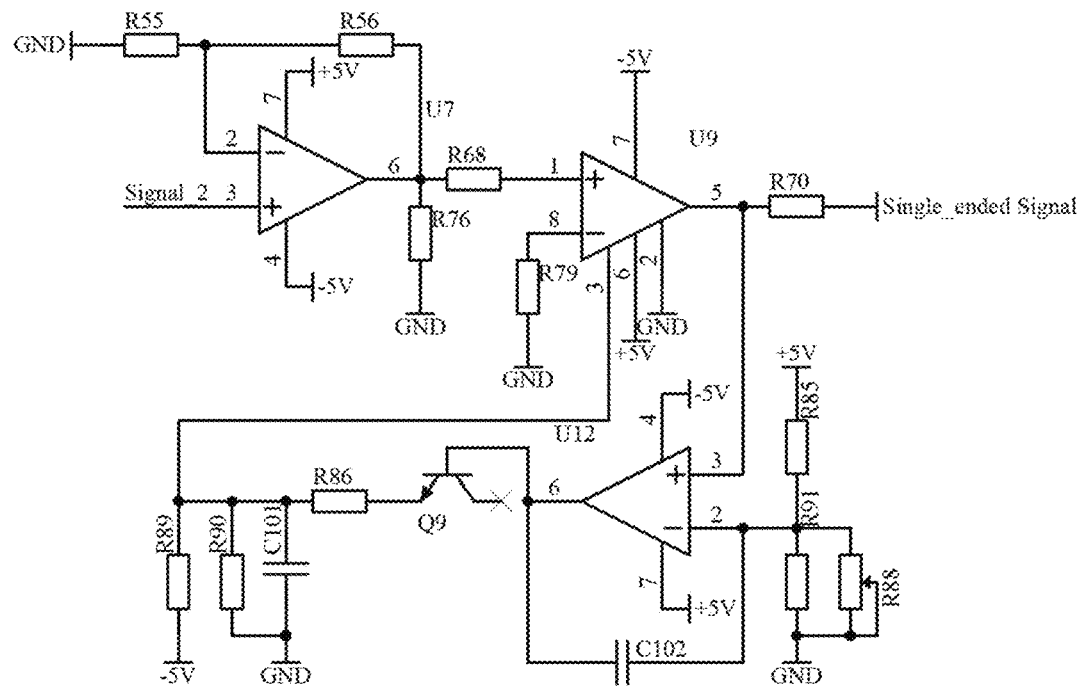
FIG. 8 is a schematic diagram of an automatic gain control circuit.

FIG. 8 shows an automatic gain control circuit in the echo signal conditioning and collection circuit, consisting of a high gain wide range adjustable gain amplifier U9, a low power consumption wide range operational amplifier U12, a low noise high speed operational amplifier U7, resistors R55, R56, R76, R68, R79, R89, R90, R86, R85, R91, R88 and R70, capacitors C101 and C102, a transistor Q9. U7 and its peripheral resistors R55, R56 form an in-phase amplifier. The resistor R76 is a pull-down resistor, the resistor R68 is a 0 ohm connection resistor. The automatic gain circuit of the echo signal is mainly achieved by U9, U10 and a negative feedback structure established by peripheral discrete devices thereof, Signal_2 is input of the feedback section, Single_ended Signal is output. If an input electrical level of pin 3 of U9 is $V_c$, real gain $G_{(dB)}$ of U9 is obtained by calculating equation (6).

$$G_{(dB)} = -40(V_C+1) \text{dB} \qquad (6)$$

It can be seen from equation (6) that the gain turns from −40 dB to +40 dB linearly when $V_c$ varies from 0V to −2V. U12 and a transistor Q9 form a peak detection circuit. Resistors R85, R91 and a slide rheostat R88 are configured to set up a peak reference voltage $V_{ref}$. The resistor R79 is a balancing resistor, and the resistor R70 is a 0 ohm connection resistor. Resistors R89 and R90 form a voltage division circuit, which provide a biasing voltage to the pin 3 of U9. The resistor R86 and capacitor C101 determine a sampling frequency of the feedback circuit. The operational process of the feedback circuit is as follows.

When a peak of Single_ended Signal is larger than $V_{ref}$, U12 outputs a forward voltage, a base emitter of a triode is turned on, the capacitor C101 is charged, the input voltage of the pin 3 of U9 generates a direct variation, gain decreases. As a result, Single_ended Signal decreases till the peak is equal to $V_{ref}$, the automatic gain circuit becomes stable.

When the peak of Single_ended Signal is smaller than $V_{ref}$, U12 outputs a negative voltage, the base emitter of the triode is turned off, at the moment, the capacitor C101 is charged by −5V, the input voltage of the pin 3 of U9 generates a negative variation, the gain increases. As a result, Single_ended Signal increases till the peak is equal to $V_{ref}$, the automatic gain circuit becomes stable.

Figure 9:
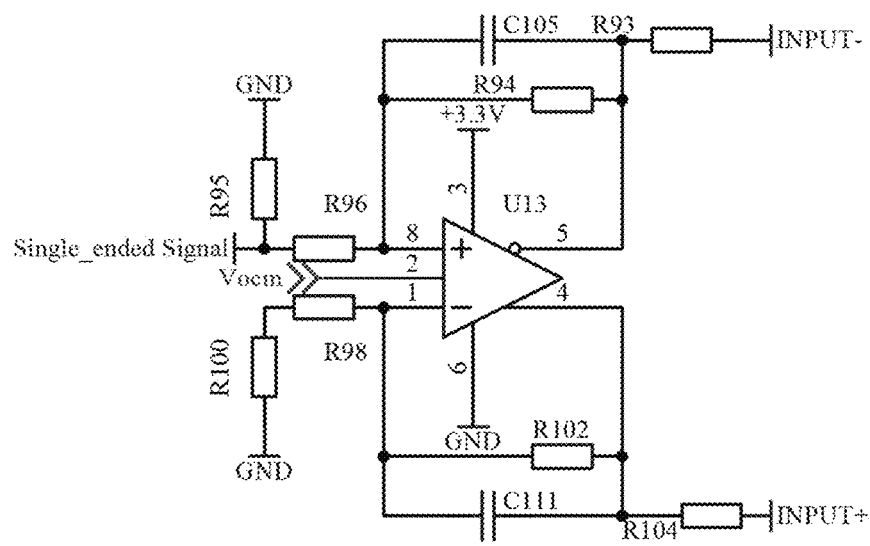
FIG. 9 is a schematic diagram of a single-ended-to-differential conversion circuit.

FIG. 9 is a single-ended-to-differential conversion circuit in the echo signal conditioning and collection circuit, consisting of a low distortion differential ADC driver U13, resistors R95, R96, R94, R93, R100, R98, R102, R104, capacitors C105 and C111. In order to achieve the optimum performance of the difference circuit, device parameters of an in-phase and an anti-phase terminal of U13 and PCB (printed circuit board) place and route all keep symmetrical if possible, which means the resistors R95, R96, R94, R93 and the capacitor C105 are symmetrical to the resistors R100, R98, R102, R104 and the capacitor C111, the resistor R94 and capacitors C105, the resistor R102 and capacitors C111 form one-order low pass filtering respectively. Which are output to the next stage circuit through the resistors R93 and R104 after the double-ended signal of differential amplification.

Figure 10:
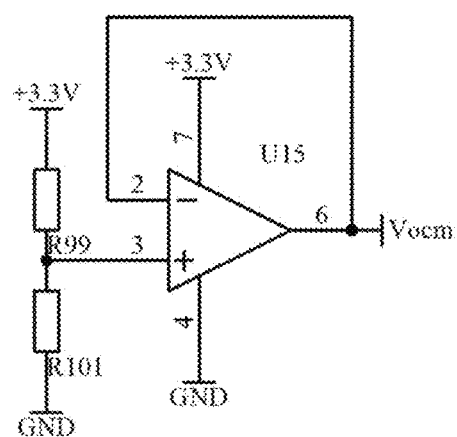
FIG. 10 is a schematic diagram of a biasing circuit.

As shown in FIG. 10, $V_{ocm}$ is a common-mode input voltage. U15 is an ordinary low noise operational amplifier. U15 and resistors R99, R101 form a biasing circuit, $V_{ocm}$ can be deployed by changing a ratio of the resistors R99 and R101.

Figure 11:
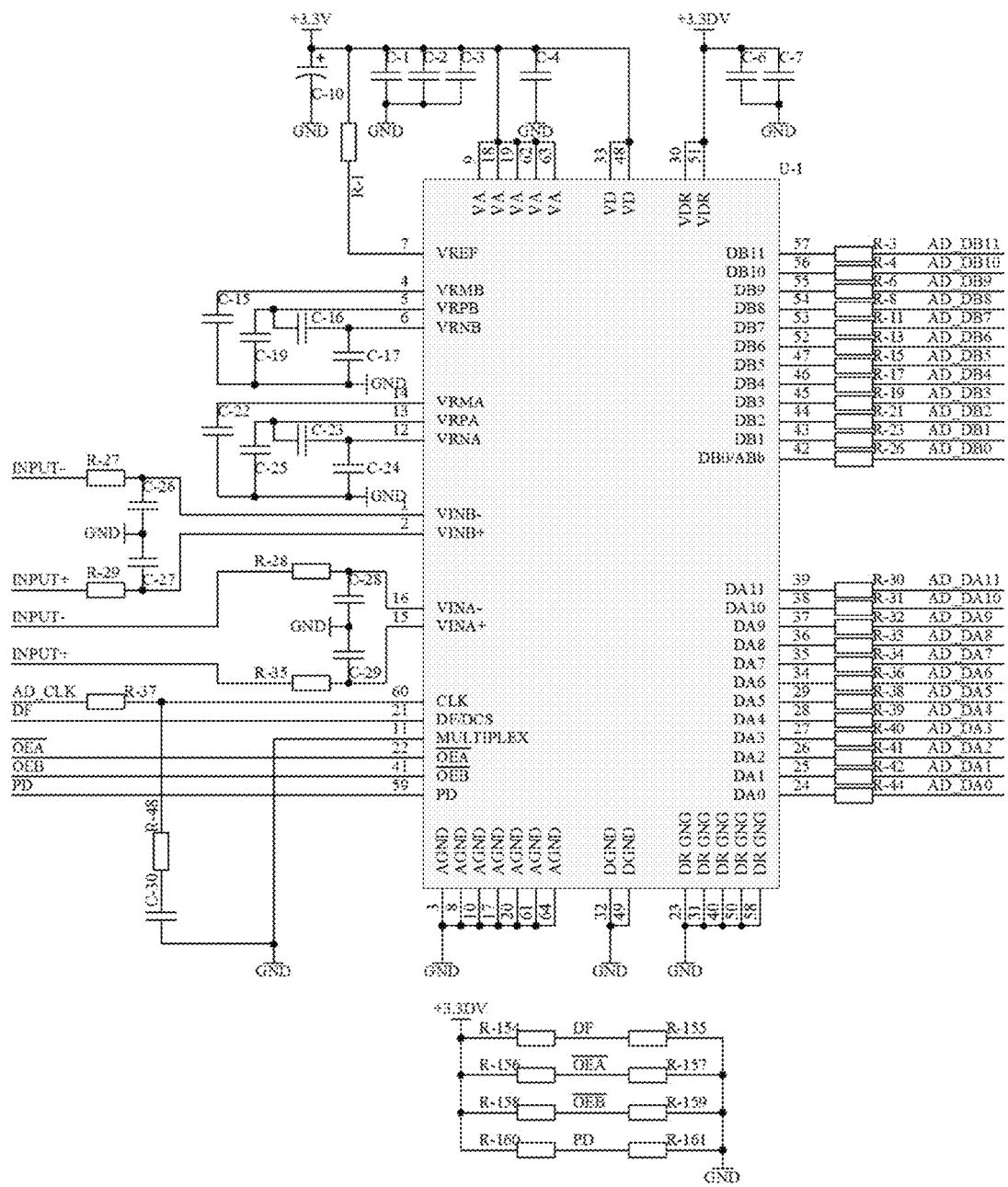
FIG. 11 is a schematic diagram of a high speed ADC signal collection and conversion circuit.

FIG. 11 is a high speed ADC signal collection and conversion circuit in the echo signal conditioning and collection circuit. The high speed ADC signal collection and conversion circuit consists of a high speed ADC chip U-1, resistors R-1, R-27, R-28, R-29, R-35, R-37, R-48, R-154, R-155, R-156, R-157, R-158, R-159, R-160, R-161, R-3, R-4, R-6, R-8, R-11, R-13, R-15, R-17, R-19, R-21, R-23, R-26, R-30, R-31, R-32, R-33, R-34, R-36, R-38, R-39, R-40, R-41, R-42 and R-44, capacitors C-15, C-16, C-17, C-19, C-22, C-23, C-24, C-25, C-26, C-27, C-28, C-29, C-30, C-1, C-2, C-3, C-4, C-6, C-7 and C-10. U-1 is a dual 12-bit pipelined. The resistor R-1 and the capacitors C-15, C-16, C-17, C-19, C-22, C-23, C-24, C-25 set the reference voltage of the high speed ADC to be 1V. The resistors R-27, R-29 and the capacitors C-26, C-27 form the first order low-pass filtering of differential input signals INPUT− and INPUT+, and connected to VINB− and VINB+ of U-1 respectively. The resistors R-28, R-35 and the capacitors C-28, C-29 also form the first order low-pass filtering of the differential input signals INPUT− and INPUT+, and connected to VINA− and VINA+ of U-1 respectively. INPUT− and INPUT+ are connected to two input terminals of two channels of U-1, redundant design enhances reliability of the system. Resistors R-154, R-155, R-156, R-157, R-158, R-159, R-160 and R-161 can deploy pin levels of DF, $\overline{OEA}$, $\overline{OEB}$ and PD, which is deploying an operational mode of U-1, A or B is gated correspondingly for conversion. AD_CLK is a clock signal that FPGA provides to U-1, the resistors R-37, R-48 and the capacitor C-30 form a filtering circuit, configured to filter clutter in the clock signal. Capacitors C-1, C-2, C-3, C-4, C-6, C-7 and C-10 are decoupling capacitors, resistors R-3, R-4, R-6, R-8, R-11, R-13, R-15, R-17, R-19, R-21, R-23 and R-26 are B channel output buffer resistors, which prevent the high frequency circuit from generating reflecting and ringing. Identically, the resistors R-30, R-31, R-32, R-33, R-34, R-36, R-38, R-39, R-40, R-41, R-42 and R-44 are A channel output buffer resistors. AD_DB0 to AD_DB11 and AD_DA0 to AD_DA11 are connected to an I/O module of the FPGA chip, which output the conversion result of U-1 to FPGA.

Figures 12, 13:
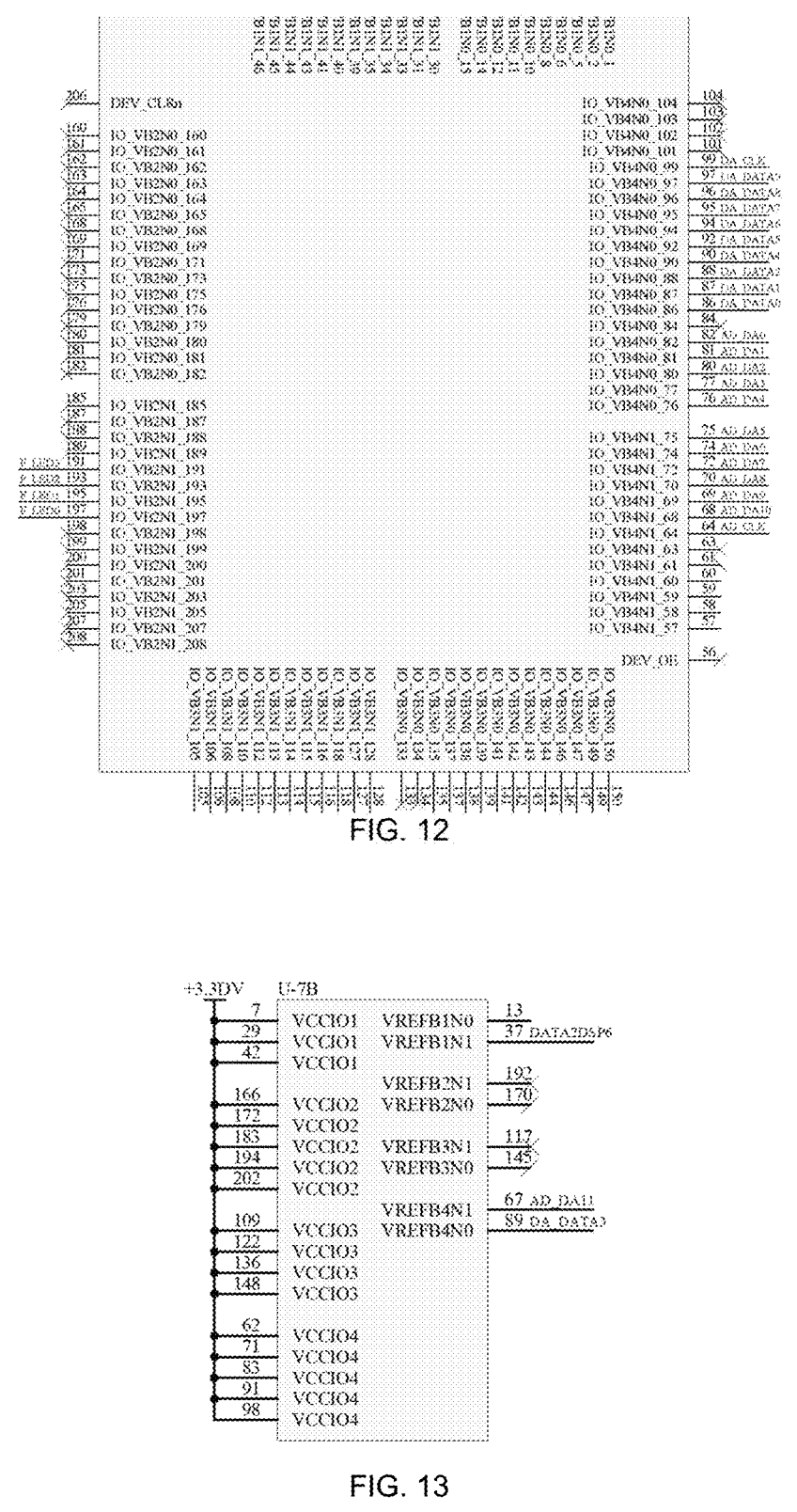
Figure 14:
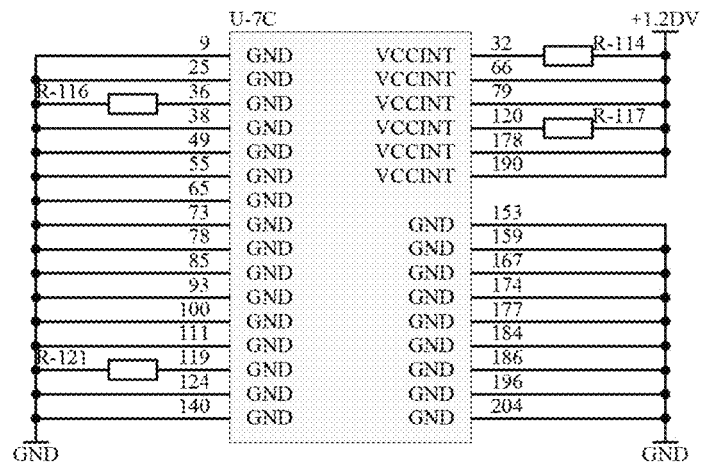
FIG. 14 is a schematic diagram of a FPGA chip (EP2C8Q208C8N) sub-module—kernel voltage and ground.
Figure 15:
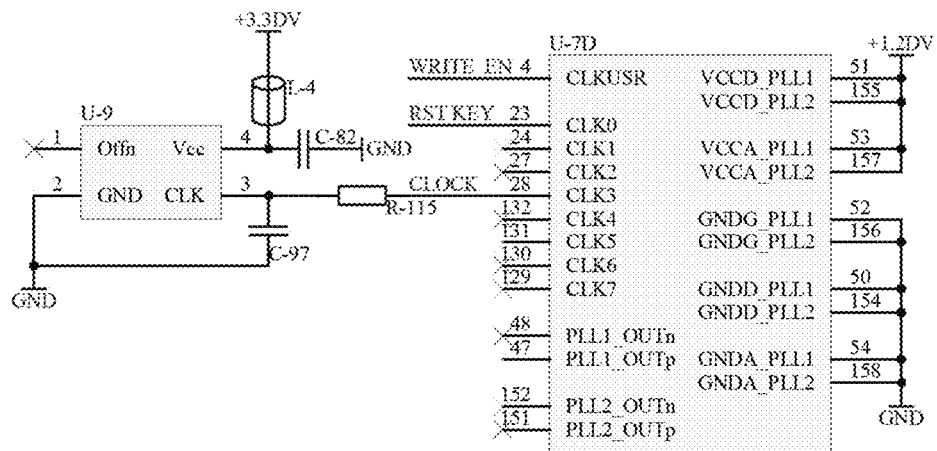
FIG. 15 is a schematic diagram of a FPGA chip (EP2C8Q208C8N) sub-module—clock input.
Figure 16:
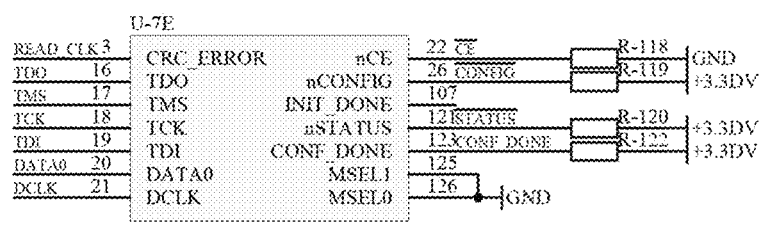
FIG. 16 is a schematic diagram of a FPGA chip (EP2C8Q208C8N) sub-module—simulation interface.
Figure 17:
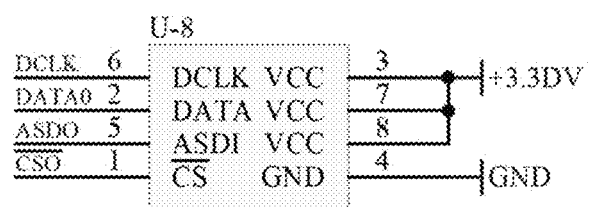
FIG. 17 is a schematic diagram of a FPGA chip serial configurator circuit.
Figure 18:
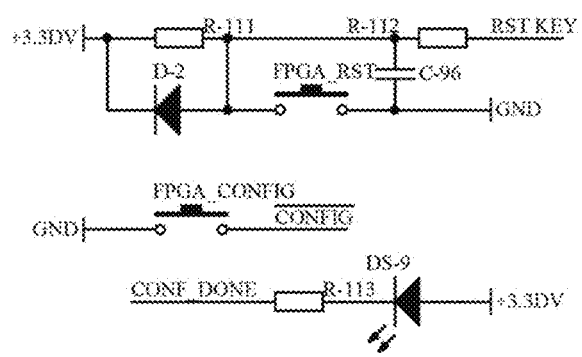
FIG. 18 is a schematic diagram of a FPGA chip reset and configuration button circuit.

FIG. 12 shows an I/O interface sub-module. FIG. 13 shows an I/O voltage and reference voltage sub-module. FIG. 14 shows a kernel voltage and ground sub-module. FIG. 15 shows a clock input sub-module. FIG. 16 shows a simulation interface sub-module. FIGS. 12, 13, 14, 15 and 16 form the FPGA circuit system, in the FPGA circuit system, a model of the FPGA chip is EP2C8Q208C8N, U-7A, U-7B, U-7C, U-7D and U-7E in FIGS. 12-16 together form the FPGA chip. FIG. 17 shows a serial configurator circuit of the FPGA chip. The FPGA chip serial configurator circuit is formed by a Flash serial configurator U-8. FIG. 18 is a reset and configuration button circuit of the FPGA chip. The FPGA reset and configuration button circuit consists of resistors R-111, R-112, R-113, a capacitor C-96, a diode D-2 and a button. The circuits above form a minimum system of an operational FPGA chip. Pins of the FPGA chip are mainly classified as 5 types as follows.

1. The first type of pins are connected to the FPGA chip power and the reference terminal of the ground. These pins are mainly centralized in circuit modules shown in FIGS. 13 and 14.

2. The second type of pins are connected to JTAG (joint test action group) terminal and the serial configurator of the FPGA chip. These pins are mainly centralized in circuit modules shown in FIGS. 16 and 17, and configured to deploy functions of the FPGA chip and guiding programs.

3. The third type of pins are connected to the reset circuit and configuration button of the FPGA chip. These pins are mainly centralized in circuit modules shown in FIG. 18, and configured to reset and deploy the FPGA chip.

4. The fourth type of pins are connected to the high speed ADC and the high speed DAC. These pins are mainly centralized in circuit modules shown in FIG. 12 and FIG. 13. DA_DATA0, DA_DATA1, DA_DATA2, DA_DATA3, DA_DATA4, DA_DATA5, DA_DATA6, DA_DATA7, DA_DATA8, DA_DATA9 and DA_CLK are connected to IO_VB4N0_86, IO_VB4N0_87, IO_VB4N0_88, VREFB4N0, IO_VB4N0_90, IO_VB4N0_92, IO_VB4N0_94, IO_VB4N0_95, IO_VB4N0_96, IO_VB4N0_97 and IO_VB4N0_99 pins of the FPGA chip, respectively, and configured to control the high speed DAC to generate driving signals by the FPGA. AD_DA0, AD_DA1, AD_DA2, AD_DA3, AD_DA4, AD_DA5, AD_DA6, AD_DA7, AD_DA8, AD_DA9, AD_DA10, AD_DA11, AD_CLK, AD_DB0, AD_DB1, AD_DB2, AD_DB3, AD_DB4, AD_DB5, AD_DB6, AD_DB7, AD_DB8, AD_DB9, AD_DB10 and AD_DB11 are connected to IO_VB4N0_82, IO_VB4N0_81, IO_VB4N0_80, IO_VB4N0_77, IO_VB4N0_76, IO_VB4N1_75, IO_VB4N1_74, IO_VB4N1_72, IO_VB4N1_70, IO_VB4N1_69, IO_VB4N1_68, VREFB4N1, IO_VB4N1_64, IO_VB3N1_105, IO_VB3N1_106, IO_VB3N1_108, IO_VB3N1_110, IO_VB3N1_112, IO_VB3N1_113, IO_VB3N1_114, IO_VB3N1_115, IO_VB3N1_116, IO_VB3N1_118, IO_VB3N1_127, IO_VB3N1_128 pins of the FPGA chip, respectively, and configured to control the high speed ADC by the FPGA chip to collect and convert echo signals in a predefined frequency, and unload the conversion result to a dual-port RAM module in the FPGA chip.

5. The fifth type of pins are connected to the DSP chip. These pins are mainly centralized in circuit modules shown in FIG. 12, FIG. 13 and FIG. 16. DA_RSTn connected to the pin IO_VB1N0_8 is configured to receive the start-to-measure command sent from the DSP chip and start the high speed DAC to output driving signals. RAM_RSTn connected to the pin IO_VB1N0_6 is configured to receive the reset command sent from the DSP chip and initiate the dual-port RAM in the FPGA chip to store data temperately. When the high speed conversion code values stored in the dual-port RAM in the FPGA chip achieves a certain amount, INT2DSP connected with the pin IO_VB1N1_46 will send a request accepted signal to the DSP chip. READ_EN connected with the pin IO_VB1N0_5 is configured to detect a read commend sent from the DSP chip, which means the DSP chip is ready for receiving data. READ_CLK connected with the pin CRC_ERROR is configured to control data transportation speed between the FPGA chip and the DSP chip. DATA2DSP0, DATA2DSP1, DATA2DSP2, DATA2DSP3, DATA2DSP4, DATA2DSP5, DATA2DSP6, DATA2DSP7, DATA2DSP8, DATA2DSP9, DATA2DSP10 and DATA2DSP11 connected with IO_VB1N1_45, IO_VB1N1_44, IO_VB1N1_43, IO_VB1N1_41, IO_VB1N1_40, IO_VB1N1_39, VREFB1N1, IO_VB1N1_35, IO_VB1N1_34, IO_VB1N1_33, IO_VB1N1_31 and IO_VB1N1_30 pins are configured to parallel transmit collected data temporarily stored in the FPGA chip to the DSP chip.

Figure 19:
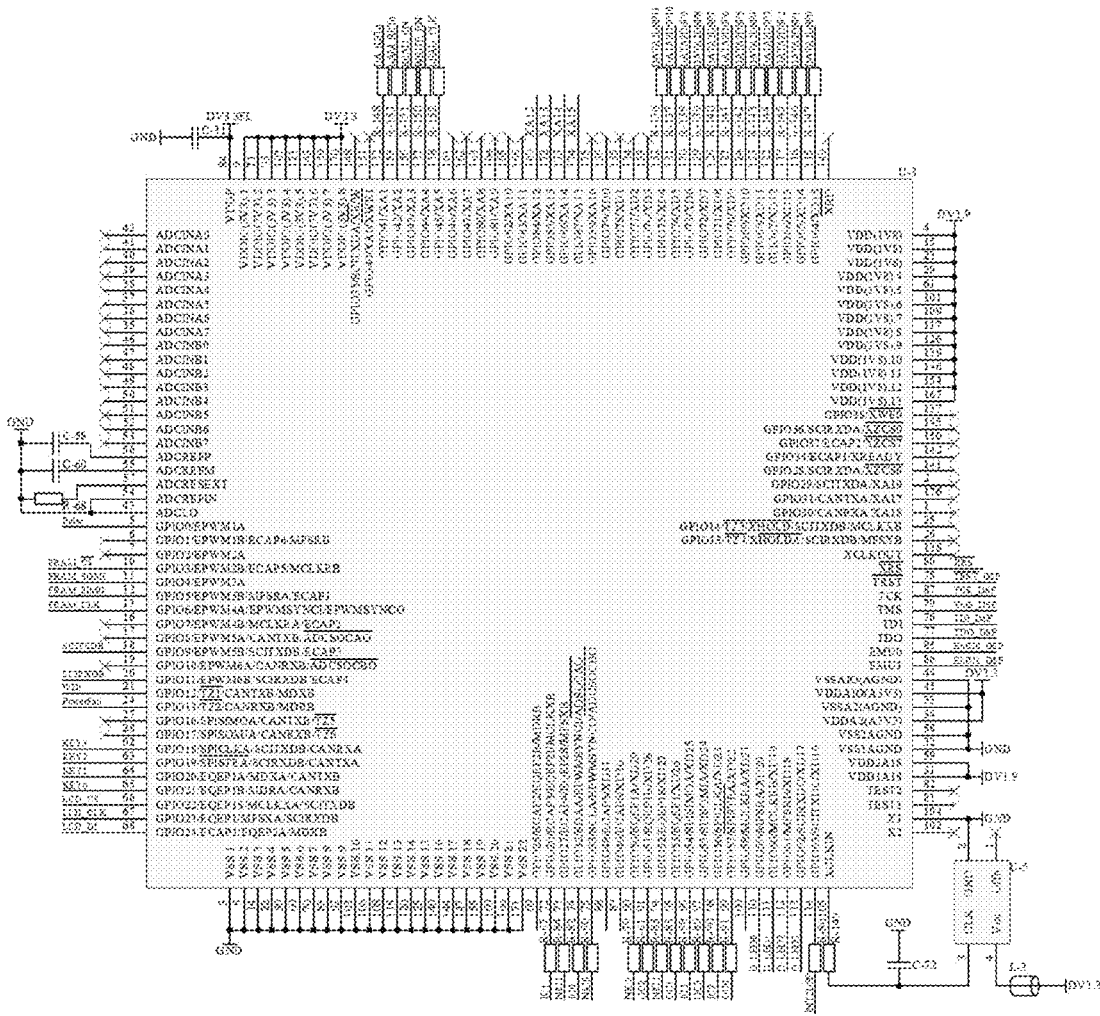
FIG. 19 is a schematic diagram of a DSP chip circuit.
Figure 20:
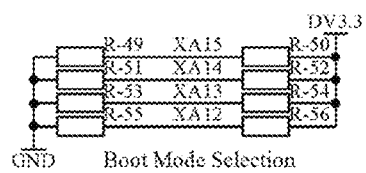
FIG. 20 is a schematic diagram of a DSP chip booting mode selection circuit.

FIG. 19 is a DSP circuit system. In the DSP circuit system, a model of the DSP chip is TMS320F28335. The DSP chip booting mode selection circuit consists of resistors R-49, R-50, R-51, R-52, R-53, R-54, R-55 and R-56, referring to FIG. 20.

Pin links of the DSP chip are mainly classified as 5 types as follows.

1. The first type of pins are connected to the DSP chip power and the reference terminal of the ground.

2. The second type of pins are connected to the DSP chip JTAG terminal. Pins 80, 78, 87, 79, 76, 77, 85 and 86 are connected to corresponding pins of the DSP chip JTAG terminal.

3. The third type of pins are connected to the transmitting/receiving signal channel switch circuits. OC0 and IC0 connected with pins 99 and 74, OC1 and IC1 connected with pins 95 and 72, OC2 and IC2 connected with pins 91 and 98, OC3 and IC3 connected with pins 97 and 96 are corresponding to channel switches of transmitting and receiving signals of the transducers 1, 2, 3, 4, respectively. As shown in FIG. 1, when the first transducer 1 is transmitting, the third transducer 3 is receiving, a corresponding channel is marked as channel A. When the second transducer 2 is transmitting, the fourth transducer 4 is receiving, a corresponding channel is marked as channel B. When the second transducer 3 is transmitting, the first transducer 1 is receiving, a corresponding channel is marked as channel C. When the fourth transducer 4 is transmitting, the second transducer 2 is receiving, a corresponding channel is marked as channel D, and such a loop can measure an ultrasonic flow. NIC0, NIC1. NIC2 and NIC3 connected with pins 75, 73, 90 and 94 are corresponding to 'non' logic signals of IC0, IC1, IC2 and IC3.

4. The fourth type of pins are connected with control and transportation of the FPGA chip. DA_RSTn connected with a pin 152 is configured to start to measure flow rates and notify the FPGA chip to initiate an external DAC module to output driving signals. RAM_RSTn connected with a pin 153 is configured to initiate temporarily stored data in the dual-port RAM in the FPGA chip. INT2DSP connected with a pin 114 is configured to notify the DSP chip to start receiving the high speed ADC conversion code values stored in the FPGA chip. READ_EN connected with a pin 156 is configured to enable reading of the dual-port RAM in the FPGA chip, the DSP chip is ready for receiving data. READ_CLK connected with a pin 158 is configured to control speed of data transportation by the DSP chip and provide clock signals for the data transportation. DATA2DSP0~DATA2DSP11 connected with pins 115, 116, 119, 122, 123, 124, 127, 128, 129, 130, 131 and 132 are configured to parallel receive collected data temporarily stored in the FPGA chip.

5. The fifth type of pins are connected with other functional modules, for instance, FRAM_$\overline{CS}$, FRAM_SOMI, FRAM_SIMO and FRAM_CLK connected with pins 10, 11, 12, 13 are configured to exchange data with the external ferromagnetic random access memory. KEY0~KEY3 connected with pins 65, 64, 63 and 62 are configured to receive external keyboard input signals. LCD_CS, LCD_CLK and LCD_DI connected with pins 66, 67 and 68 are configured to control display of an external liquid crystal module. SCITXDB and SCIRXDB connected with pins 18 and 20 are configured to serially communicate with the host computer.

The DSP chip booting mode selection circuit can modify a booting mode of the DSP chip by deploying resistance ratios of R-49 and R-50, R-51 and R-52, R-53 and R-54 as well as R-55 and R-56.

Figure 21:
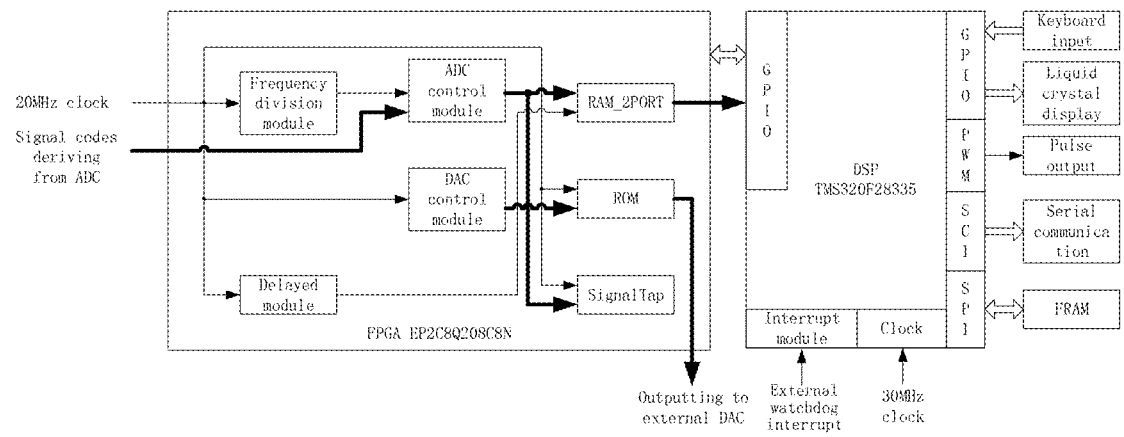
FIG. 21 is a schematic diagram of functional module of time sequential controlling and signal processing circuit.

FIG. 21 shows a schematic diagram of a functional module of a time sequential controlling and signal processing circuit. The FPGA chip adopts a design method of Top-Down, dividing functions and designing structures from top. Main functional modules of the FPGA chip include a frequency division module, an ADC control module, an RAM_2PORT module, a DAC control module, a ROM module, a delay module and a SignalTap module, each module adopts a synchronous design scheme. The frequency division module is configured to modulate 20 MHz clock signals input from outside to be 5 MHz sampling clock output to the high speed ADC. The ADC control module is configured to move the conversion code values of the high speed ADC to the RAM_2PORT module in the FPGA chip. The RAM_2PROT module is configured to store the high speed ADC conversion code values, when storage of the conversion code values of the high speed ADC achieves a certain amount, the DSP chip receives a ready-to-read signal, the stored high speed ADC conversion code values are transported to the DSP chip in accordance with a certain speed. The DAC control module is configured to move the waveform data stored in the ROM module to the high speed DAC to generate a corresponding excitation waveform. The delay module is configured to control the RAM_2PROT module to start storing the conversion code values of the high speed ADC undergoing predefined delayed time after excitation signals are sent for saving storage space. The SignalTap module is mainly configured to observe the conversion code values of the high speed ADC in real time after downloading programs for convenience of program modification and adjustment.

Six functional modules integrated in the DSP chip are a GPIO module, an interrupt module for the external watchdog interrupt, a PWM (pulse width modulation) module, a SCI (serial communication interface) module, a SPI (serial peripheral interface) module and a clock module, which are shown in FIG. 21. The DSP chip receives the high speed ADC conversion code values stored in the FPGA chip by a GPIO module. Moreover, one GPIO of the DSP chip is connected to the FPGA chip as a data latch signal. The DSP chip enables the data latch signal after receiving the ready-to-read signal sent by FPGA and reads one conversion code value of the high speed ADC in the FPGA chip. Simultaneously, an indicator in the FPGA chip shifts down 1 line, the manipulation above is repeated until all the data stored in the FPGA chip is read. After reading, the DSP chip sends a reset command to the FPGA chip to clear data in RAM_2PORT space and the delayed module in the FPGA chip and get ready for next measurement. Moreover, the GPIO module of the DSP chip accomplishes keyboard input and liquid crystal display. The PWM module accomplishes pulse output of flow results to demarcate later gas flow rates. The SCI module accomplishes serial communication with the host computer to store and analyze flow results. An SPI module accomplishes a bidirectional read-write with the ferromagnetic random access memory FRAM, when the DSP chip detects power-off reset, the DSP chip writes the accumulated flow rates and the meter parameters in FRAM. The system selects an external watchdog to prevent the program from running. Moreover, the external watchdog further has functions such as button reset, power-on/power-off reset and low voltage monitor.

Figure 22:
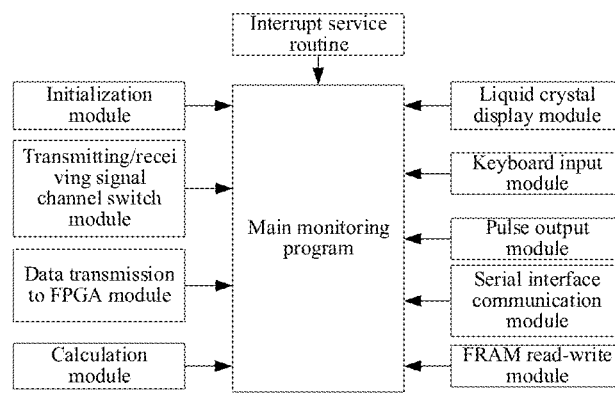
FIG. 22 is a software block diagram of the DSP chip.

FIG. 22 shows a software block diagram of the DSP chip. The software design adopts a modularized design method. The software consists of a main monitoring program and various subroutine modules. The main monitoring program is a master scheduling program, the various subroutine modules include an initialization module, a transmitting/receiving signal channel switch module, a data transmission to FPGA module, an interrupt service routine, a calculation module, a FRAM read-write module, a serial interface communication module, a pulse output module, a keyboard input module, and a liquid crystal display module. The main monitoring program is a master scheduling program of the entire system, which implements each function of the ultrasonic gas flow meter transmitter by calling each subroutine module.

Figure 23:
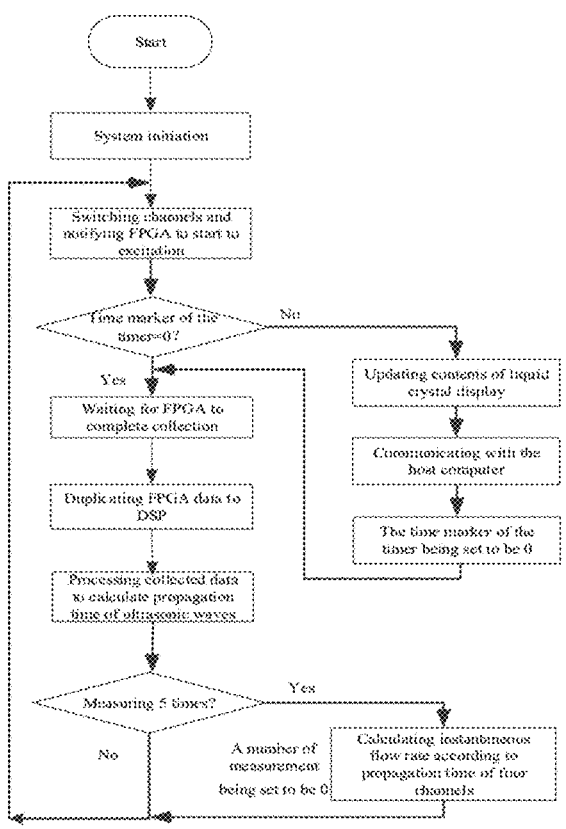
FIG. 23 is a flowchart of a main monitoring program.

FIG. 23 is a flowchart of a main monitoring program of the circuit system. The main monitoring program operates automatically after the circuit system is powered. Specific manipulation steps of the main monitoring program are as follows.

(1) Initialization of the Circuit System

After the circuit system is powered, the DSP chip accomplishes initialization of each section: including assigning GPIO ports of the DSP chip, interrupt initialization of an internal timer 1 of the DSP chip, initializing the liquid crystal display module, reading accumulated flow rates in the FRAM read-write module, initializing each parameter of the meter, and creating 4 queues, each of the queues consists of 50 digital space vacancies, configured to store the propagation time of ultrasonic waves received by 4 transducers (short for propagation time in the following). Whenever one new propagation time data enters, data on the front of each of the queues will be abandoned, the new propagation time data is added on the end of the queue, in a subsequent measuring process, average downstream and upstream propagation times of dual channel ultrasonic flow meter will be calculated in real time according to data of the 4 queues.

(2) Circulation of Flow Measurement

The program enters circulation of flow measurement after the circuit system is initiated. Firstly the DSP chip switches transmitting and receiving channels of transducers by changing output status of corresponding GPIO ports. Order of switching channels is: the first transducer 1 transmits while the third transducer 3 receives, the second transducer 2 transmits while the fourth transducer 4 receives, the third transducer 3 transmits while the first transducer 1 receives, and the fourth transducer 4 transmits while the second transducer 2 receives. Switching processes above are cycled continuously. The FPGA chip is noticed to measure after switching channels, the DSP chip needs to wait for the FPGA chip to receive signals.

(3) The FPGA Chip Controls the High Speed DAC and the High Speed ADC to Accomplish Signal Driving and Collection of Echo Signals.

After switching channels, the DSP chip sends a start-to-measure signal to the FPGA chip, the FPGA chip immediately enables an internal delayed module, and waveform data stored in a ROM module in the FPGA chip is called simultaneously to be transferred to the driving signal generation and amplification circuit, then output to the first transducer 1, or the second transducer 2, or the third transducer 3, or the fourth transducer 4 of a direct injection dual channel structure through the transmitting/receiving signal channel switch circuits controlled by the DSP chip, the first transducer 1, or the second transducer 2, or the third transducer 3, or the fourth transducer 4 emits ultrasonic waves. The ultrasonic waves arrive at a corresponding receiving transducer after some propagation time. The third transducer 3, or the fourth transducer 4, or the first transducer 1, or the second transducer 2 receives the ultrasonic waves to form an echo signal. The transmitting/receiving signal channel switch circuits controlled by the DSP chip receive the echo signal emitted from the transducers and input the echo signal to the echo signal conditioning and collection circuit. The high speed ADC in the echo signal conditioning and collection circuit accomplishes data conversion. RAM_2PORT module in the FPGA chip is configured to temporarily store the conversion code values of the high speed ADC, when predefined time determined by a delayed circuit is up, the preset GPIO port of the DSP chip is pulled up to notify the DSP chip completion of signal collection.

(4) Data Duplication

The DSP chip duplicates the data stored in the RAM_2PORT module in the FPGA chip to the RAM in the DSP chip after detecting a high level of a preset terminal, so as to provide the DSP chip for processing digital signals.

There is waiting time of around 400 μs before the DSP chip is aware of completion of signal collection. The period is time for ultrasonic waves to propagation in the channel, and time for the FPGA chip to receive the collected signals. In the period, the DSP chip can complete update of the liquid crystal display, as well as communication with the host computer. Not each signal collection comes along with update of the liquid crystal display and communication with the host computer, which is done once a second, controlled by a time marker in the timer 1 in the DSP chip. The DSP chip firstly judges if the time marker of the timer 1 is 0 or not. If it is not 0, the two missions will be completed, subsequently, the time marker of the timer is set to be 0. If it is 0, no mission will be processed. The time marker of the timer 1 will be set to be 1 in the interrupt service routine once a second. The waiting time is utilized thoroughly by the time marker of the timer 1 to improve real-time of the system.

(5) The DSP Chip Processing the Data, Calculating the Propagation Time of the Ultrasonic Waves The DSP chip processes the duplicated data, the propagation time of each of the ultrasonic waves is calculated.

Figure 24:
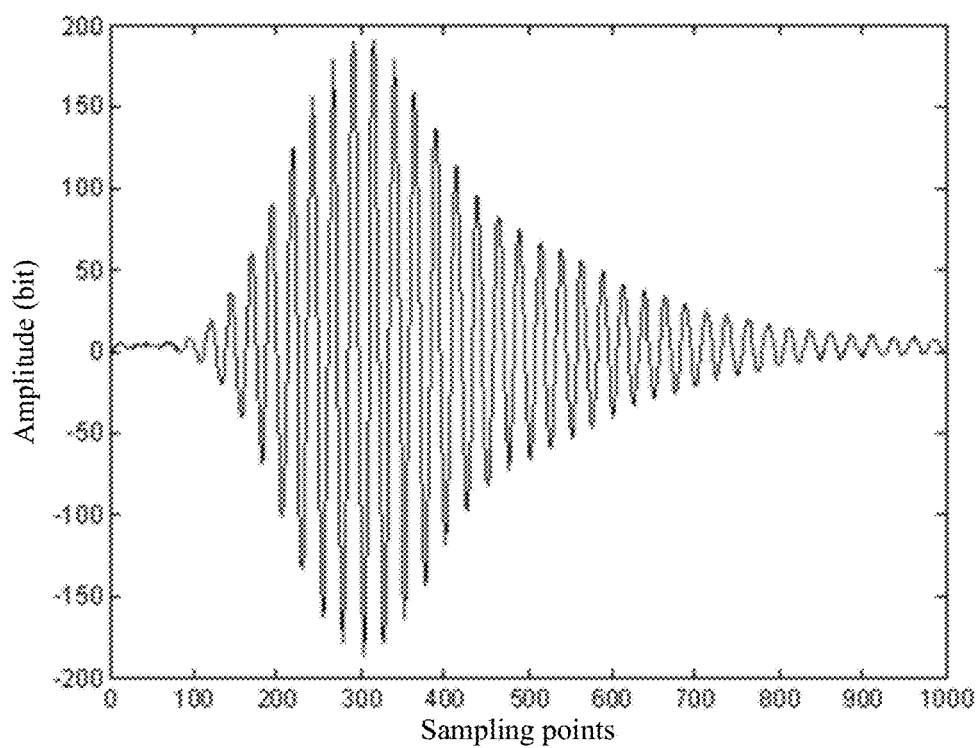
FIG. 24 is a waveform view of an echo signal.
Figure 25:
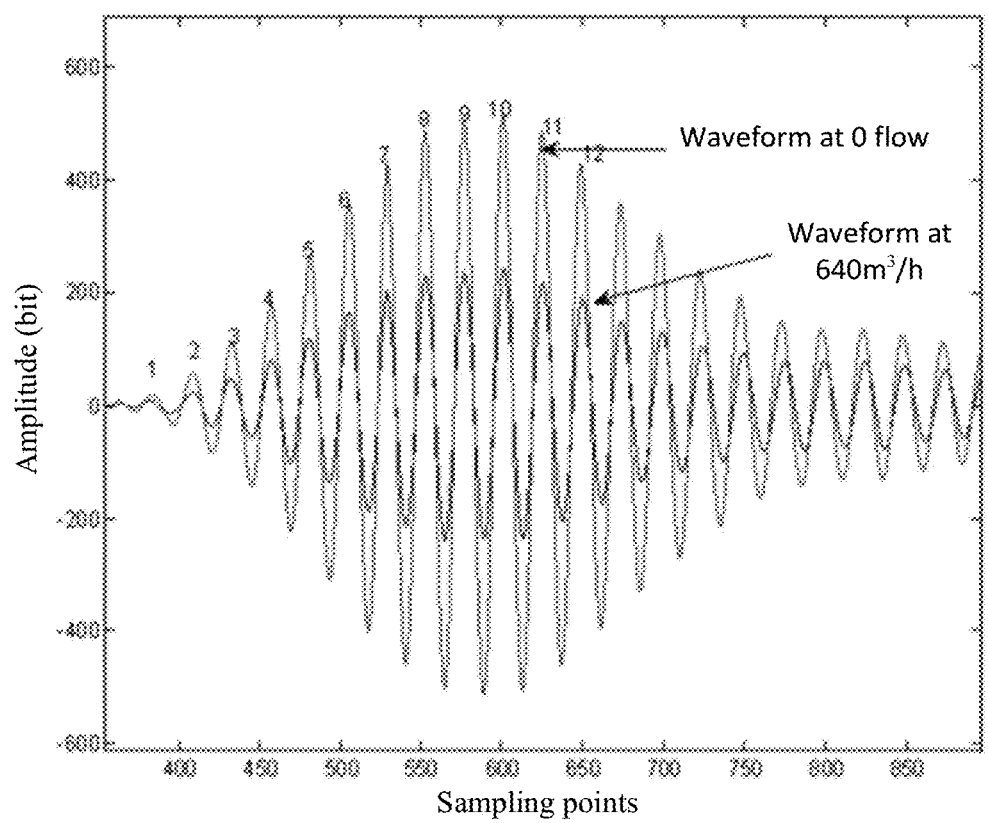
FIG. 25 is comparison view of echo signal waveforms in various flow rates.

Received echo signal waveform is as shown in FIG. 24. The signal waveform is similar to a sine wave with modulated amplitude, which has multiple waves. Peaks of each of the waves are firstly ascending and then descending to zero. The collected signals are firstly digital filtering, a fourth-order bandpass IIR digital filter with a cut-off frequency of 200 kHz±80 kHz is adopted. The noise in the echo signals is reduced after filtering. Waveforms of signals with 0 flow and 640 $m^3/h$ after filtering are aligned and drew in an identical picture, which is shown as FIG. 25. It can be seen that shapes of the echo signals in the two flow rates are almost the same, therefore, ratios of each peak in the waves and the maximum peak in the echo signals should be basically identical as well. The feature of the echo signals can be utilized to find out a certain feature wave accurately. First, a maximum peak $A_{max}$ in the filtered echo signals is found out, a variable ratio threshold SW(SW=$\alpha \cdot A_{max}$) is set up according to the maximum peak. $\alpha$ is a constant value, which is obtained by statistical calculation ahead. The transducer corresponding to FIG. 25 is taken as an example, in the flow range of 0~800 $m^3/h$, one flow point is picked every 100 $m^3/h$, 50 echo signals in every flow point are collected, subsequently, MATLAB is utilized to analyze, the ratios of each peak and the maximum peak in the echo signals are calculated. It can be seen that in each flow rate, a ratio of the fifth wave, the sixth wave and the maximum peak is basically constant. A ratio of peak of the fifth wave and the maximum peak keeps around 0.39, a ratio of peak of the sixth wave and the maximum peak keeps around 0.53. Therefore, $\alpha$ is an average value of the two, which is 0.46. The echo signals are detected by SW, when the amplitude of the echo signals first achieves the threshold, the corresponding wave is the wanted feature wave. The method of determining the feature wave in the echo signals is called the variable ratio threshold method.

The feature wave found out accurately by the variable ratio threshold method can be depended on to calculate the required zero-crossing point. Eight zero-crossing points behind the feature wave are adopted, propagation time is calculated by an average value of the 8 points to eliminate some random errors, which improves accuracy in measurement. Arranged by time sequence, time corresponding to the eight zero-crossing points is $\tau_1, \tau_2 \ldots \tau_8$, respectively.

Figure 26:
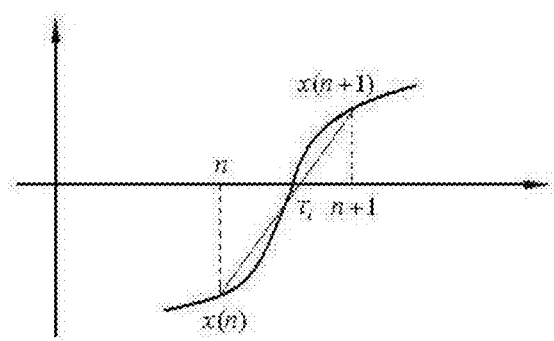
FIG. 26 is a linear interpolation calculating a zero-crossing point.

The feature wave found out accurately by the zero-crossing method of variable ratio threshold method can be depended on to calculate the required zero-crossing point. Eight zero-crossing points behind the feature wave are adopted, propagation time is calculated by an average value of the 8 points to eliminate some random errors, which improves accuracy in measurement. Arranged by time sequence, time represented by the eight zero-crossing points is $\tau_1, \tau_2 \ldots \tau_8$, respectively. A method of linear interpolation is adopted to determine a zero-crossing point, as shown in FIG. 26. If the amplitude of a nth point is x(n), amplitude of a (n+1)th point is x(n+1), polarities of x(n) and x(n+1) are opposite, there must be a zero-crossing point between the nth point and the (n+1)th point, an equation (7) can be utilized to calculate zero-crossing points $\tau_i$(i=1, 2, 3 . . . 8) by linear interpolation.

$$\tau_i = \left(n + \frac{-x(n)}{x(n+1) - x(n)}\right)T_c \qquad (7)$$

where $T_c$ is a periodicity of collecting signals, as the sampling frequency is 5 MHz, $T_c$=0.2 μs, n is a serial number corresponding to an ith zero-crossing point. x(n) and x(n+1) are amplitudes of the nth point and the (n+1)th point respectively.

In the ultrasonic gas flow meter, if the propagation time of the ultrasonic wave in the medium is long, time of the 8 zero-crossing points is correspondingly long. Time corresponding to the 8 zero-crossing points and the propagation time of ultrasonic waves are linearly related, therefore, the propagation time T can be calculated by the equation (4):

$$T = 1/8 \Sigma_{i=1}^{8} \tau_i - t' \qquad (4)$$

where $\tau_i$(i=1, 2, 3 . . . 8) is zero-crossing time calculated by the equation (7), t' is a stationary deviation value, the deviation value can be obtained by calculating at zero flow rate.

During the gas does not flow in the pipeline, first, the propagation time $T_0$ of the ultrasonic echo wave is calculated by a measured length of the channel and the actual sound velocity, time $\tau_{0i}$(i=1, 2, 3 . . . 8) corresponding to 8 zero-crossing points is calculated according to the equation (7), finally, the stationary deviation value t' is calculated by an equation (8).

$$t' = 1/8 \sigma_{i=1}^{8} \tau_{0i} - T_0 \qquad (8)$$

The propagation time of ultrasonic waves can be calculated in real-time according to equations (7) and (4) after obtaining t'.

Calculating an Instantaneous Flow Rate

One propagation time of the ultrasonic waves from a transducer to another transducer is obtained by one circulation of steps (2)~(5).

Different transmitting transducers and receiving transducers are switched in step (2) to measure the propagation time of each downstream and upstream propagating channel successively in sequence; after four loops as such measurement of the propagation time of downstream and upstream propagating dual channel is accomplished, the four propagation time is placed in the 4 queues created in the step (1) respectively.

Five times of such measurement are preformed to calculate the average downstream and upstream propagation times of dual channels, an average flow rate is calculated as an instantaneous flow rate to be displayed according to the average propagation time.

Figure 27:
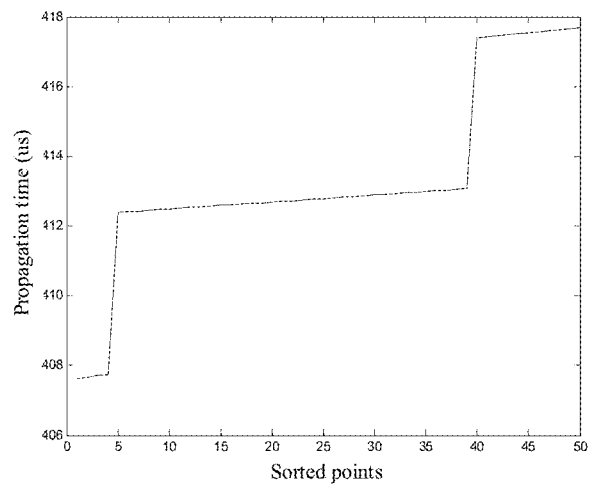
FIG. 27 is a stair-like schematic view appearing along with calculation mistakes.

In order to improve stability of the system in measurement and appearance of gross errors in extreme situations, a method of judging stair is adopted, which is taking 50 data out of a propagation time queue corresponding to one channel, the data is stored in other established arrays, subsequently, data representing propagation time of 50 measurements is arranged in a sequence from small to large during calculating the average flow rate. If gross errors occur in the 50 measurement results, in that way, arranged propagation time values will appear an obvious stair phenomenon, as shown in FIG. 27. Data is divided in several sections by judging the stair, a section with the most points is accurate propagation time data. FIG. 27 is taken as an example, the stair appears in the fifth point and the fortieth point, the 50 propagation time data is divided in 3 subsections—1~4 points, 5~39 points and 40~50 points. The 5~39 section with the most points is accurately measured propagation time. Subsequently, an average value of the accurate propagation time data is the average propagation time t of the channel.

The average propagation time $t_1$, $t_2$, $t_3$ and $t_4$ of the four channels are calculated, an instantaneous flow rate Q can be obtained according to equation (5).

$$Q = \frac{\pi D^2}{4} \frac{L}{2\cos\theta} \frac{\Delta t}{t_s t_n} = k_f \frac{\Delta t}{t_s t_n} \tag{5}$$

where Q is a measured instantaneous flow rate, D is a diameter of a pipe, L is a length of the channel, θ is an angle of a channel angle (an angle between a propagation path of ultrasonic waves and a pipe axis), $t_s$, $t_n$ and Δt are downstream propagation time, upstream propagation time and a time difference of them, respectively; $k_f$ is a meter parameter. It can be seen that Q is proportional to $\Delta t/t_s t_n$. $k_f$ is achieved by a calibration experiment. Time differences Δt and $t_s t_n$ are calculated according to $t_1$, $t_2$, $t_3$ and $t_4$, shown as equations (9) and (10) respectively.

$$\Delta t = 1/2(t_1 - t_3 + t_2 - t_4) \tag{9}$$

$$t_u t_d = 1/2(t_1 t_3 + t_2 t_4) \tag{10}$$

In the beginning of the calibration, an original value of a meter parameter is given initially, a flow point (i.e. around 400 m³/h) is marked, an accurate $k_f$ is achieved by correcting meter parameters according to a relationship between measured values and standard values.

Flow rates can be calculated according to equations (7), (4) and (5) after determining $k_f$. As influence of factors such as flow distribution, sound propagation path variation, the actual flow rate and $t_s t_n$ are non-linearly related. In order to reduce non-linear errors, the errors are corrected in sections according to real flow calibration results. Eleven flow points 30, 60, 80, 100, 200, 300, 400, 500, 600, 700 and 800 m³/h are selected in flow rates of 30~800 m³/h for calibration, a relation curve of the flow and the errors is obtained after achieving the errors of the flow points. The relation curve is divided and linearized to calculate an error corresponding to any flow point in 30~800 m³/h, a flow value of measurement can be corrected. The measured flow value is supposed to be Q', the error corresponding to the flow point is e(Q'), the instantaneous flow rate Q after correction is:

$$Q = Q' - Q' \cdot e(Q') \tag{11}$$

(7) Calculating Accumulated Flow Rate

Figure 28:
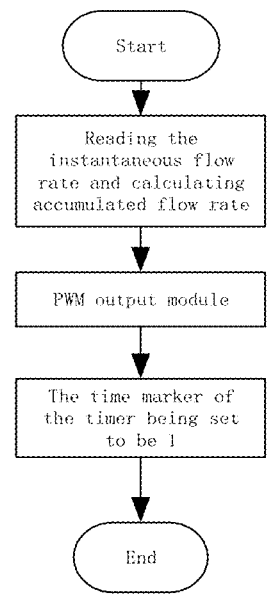
FIG. 28 is a flowchart of a timer interrupt service routine.

An interrupt service program in the internal timer 1 of the DSP chip calculates accumulated flow rate after achieving the revised instantaneous flow rate to ensure accumulation once a second, which means the timer interrupt is generated by the DSP chip internal timer 1, a period is 1 second. FIG. 28 is a flowchart of an interrupt service routine of the timer 1 in the DSP chip. A timer interrupt service routine firstly reads a result of the instantaneous flow rate calculated by the main monitoring program and accumulates to achieve the accumulated flow rate. A parameter of the pulse output module is updated according to a value of the instantaneous flow rate, pulse with certain frequency is output to represent the measured instantaneous flow rate. Subsequently, a time marker of the timer is set to be 1 to update liquid crystal display in the main monitoring program and process host computer communication.

What is claimed is:

1. An ultrasonic gas flow meter transmitter based on FPGA and DSP, wherein the ultrasonic gas flow meter transmitter consists of ultrasonic gas transducers and sensor components, transmitting/receiving signal channel switch circuits, a driving signal generation and amplification circuit, an echo signal conditioning and collection circuit, a time sequential controlling and signal processing circuit, a man-machine interface, a serial communication module and a power management module;

the ultrasonic gas transducers and sensor components are fixed on a gas pipeline;

the driving signal generation and amplification circuit consists of a high speed DAC signal generation and output circuit, a driving signal voltage and power amplification circuit;

the echo signal conditioning and collection circuit consists of a voltage amplification circuit, a bandpass filter circuit, an automatic gain control circuit, a single-ended-to-differential conversion circuit, a biasing circuit and a high speed ADC signal collection and conversion circuit;

the time sequential controlling and signal processing circuit consists of a FPGA circuit system and a DSP circuit system, the FPGA circuit system mainly consists of a FPGA chip, a FPGA chip serial configurator circuit, and a FPGA chip reset and configuration button circuit; the DSP circuit system mainly consists of a DSP chip and a DSP chip booting mode selection circuit.

2. The ultrasonic gas flow meter transmitter based on FPGA and DSP according to claim 1, wherein the ultrasonic gas transducers and sensor components consist of four transducers, a pressure sensor and a temperature sensor, each of the transducers acts as a transmitting transducer as well as a receiving transducer.

3. The ultrasonic gas flow meter transmitter based on FPGA and DSP according to claim 2, wherein the transmitting/receiving signal channel switch circuits consist of excitation strobe circuits, transformer amplification circuits and four echo strobe circuits; the four echo strobe circuits have the same structure, and connected with the transducers, respectively.

4. The ultrasonic gas flow meter transmitter based on FPGA and DSP according to claim 1, wherein the FPGA chip is configured to temporarily store a conversion code value sent by the echo signal conditioning and collection circuit, the conversion code value will be transmitted to the DSP chip when delayed time is reached; the DSP chip is a master control chip, responsible for processing digital signals, human-computer Interaction and serial communication, and cooperated with the FPGA circuit system to control time sequence of the entire system; the DSP chip adopts digital filtering to eliminate noise in signals, a variable ratio threshold and zero-crossing detection method of tracking maximum peak of the echo signal is adopted to calculate a propagation time of an ultrasonic echo, so as to obtain gas flow rates.

5. The ultrasonic gas flow meter transmitter based on FPGA and DSP according to claim 3, wherein the high speed DAC signal generation and output circuit consists of a dual differential line driver U-2, resistors R-2, R-9, R-5, R-7, R-10, R-12, R-14, R-16, R-18, R-20, R-22, R-24, R-25, capacitors C-11, C-12, C-13, C-14, C-18, C-20 and C-21; the high speed DAC signal generation and output circuit will output a high speed current signal to curb reflection and vibration;

the driving signal voltage and power amplification circuit consists of a low noise high speed operational amplifier U1, the dual differential line driver U2, resistors R13, R14, R15, R16, R17, R22, R27, R28, R29, R30, R31, R32, R33, R35, R44, capacitors C25 and C26;

the dual differential line driver U2 outputs through two channels to reinforce ability of power amplification; driving signals after voltage and power amplification are finally transmitted to a next level.

6. The ultrasonic gas flow meter transmitter based on FPGA and DSP according to claim 3, wherein the excitation strobe circuits comprise four bipolar operational amplifiers U3A, U3B, U3C and U3D; the transformer amplification circuits consist of transformers T1, T2, T3 and T4, turn ratios of T1, T2, T3 and T4 are 1:10;

the four echo strobe circuits have the same structure; each of the echo strobe circuits consists of a dual low impedance single-pole single-throw switch U4, resistors R47, R48, R49 and R50, an IC1 terminal and an NIC1 terminal of the dual low impedance single-pole single-throw switch U4 are a strobe signal and a cut-off signal of a transducer output from DSP; when IC1 is set to be high, S1 and D1 are gated, which access COM1 to the succeeding echo signal conditioning and collection circuit; JUMP1 is an adjusting terminal; the resistors R48, R49 and R50 are pull-down resistors; gated echo signals are output to succeeding circuits through the resistor R47.

7. The ultrasonic gas flow meter transmitter based on FPGA and DSP according to claim 3, wherein in the echo signal conditioning and collection circuit, the voltage amplification circuit consists of a low noise high speed operational amplifier U10, capacitors C98, C100, resistors R59, R63, R64, R77, R81, R78 and R83, the resistors R77, R81 and the low noise high speed operational amplifier U10 form an anti-phase amplification circuit; the resistors R78, R83 and the low noise high speed operational amplifier U10 form an in-phase amplification circuit;

the bandpass filter circuit consists of a 4-order continuous time active power filter U8, resistors R60, R62, R66, R67, R71, R72, R74, R75, R65 and R57, capacitor C99; a center frequency, a bandwidth, a quality factor and a gain parameter of the filter are changed by adjusting a peripheral resistors R60, R66, R71, R74, R62, R67, R72 and R75; the resistor R65 leads the echo signal after front-end conditioning to the filter, the resistor R57 and the capacitor C99 form a high pass filter;

the automatic gain control circuit consists of a high gain wide range adjustable gain amplifier U9, a low power consumption wide range operational amplifier U12, a low noise high speed operational amplifier U7, resistors R55, R56, R76, R68, R79, R89, R90, R86, R85, R91, R88 and R70, capacitors C101 and C102, a transistor Q9; U7 and its peripheral resistors R55, R56 form an in-phase amplifier; the resistor R76 is a pull-down resistor, the resistor R68 is a 0ohm connection resistor; automatic gain of the echo signal is achieved by U9, U10 and a negative feedback structure established by peripheral discrete devices thereof;

the single-ended-to-differential conversion circuit consists of a low distortion differential ADC driver U13, resistors R95, R96, R94, R93, R100, R98, R102, R104, capacitors C105 and C111, the resistors R95, R96, R94, R93 and the capacitor C105 are symmetrical to the resistors R100, R98, R102, R104 and the capacitor C111, the resistor R94 and capacitors C105, the resistor R102 and capacitors C111 form one-order low pass filtering respectively, $V_{ocm}$ is a common-mode input voltage;

the biasing circuit consists of an ordinary low noise operational amplifier U15, resistors R99 and R101;

the high speed ADC signal collection and conversion circuit consists of a high speed ADC chip U-1, resistors R-1, R-27, R-28, R-29, R-35, R-37, R-48, R-154, R-155, R-156, R-157, R-158, R-159, R-160, R-161, R-3, R-4, R-6, R-8, R-11, R-13, R-15, R-17, R-19, R-21, R-23, R-26, R-30, R-31, R-32, R-33, R-34, R-36, R-38, R-39, R-40, R-41, R-42 and R-44, capacitors C-15, C-16, C-17, C-19, C-22, C-23, C-24, C-25, C-26, C-27, C-28, C-29, C-30, C-1, C-2, C-3, C-4, C-6, C-7 and C-10;

the echo signal conditioning and collection circuit outputs a conversion result of the ADC driver U13 to the FPGA circuit system of the time sequential controlling and signal processing circuit.

8. The ultrasonic gas flow meter transmitter based on FPGA and DSP according to claim 3, wherein in the time sequential controlling and signal processing circuit, in the FPGA circuit system, a model of the FPGA chip is EP2C8Q208C8N; the FPGA chip serial configurator circuit is formed by a Flash serial configurator U-8; the FPGA reset and configuration button circuit consists of resistors R-111, R-112, R-113, a capacitor C-96, a diode D-2 and a button; the FPGA chip is formed by U-7A, U-7B, U-7C, U-7D and U-7E;

in the DSP circuit system, a model of the DSP chip is TMS320F28335; the DSP chip booting mode selection circuit consists of resistors R-49, R-50, R-51, R-52, R-53, R-54, R-55 and R-56;

in operation, the DSP chip sends a start-to-measure signal to the FPGA chip, the FPGA chip immediately enables an internal delayed module, and waveform data stored in the FPGA is called simultaneously to be transferred to the driving signal generation and amplification circuit, then output to the four transducers through the transmitting/receiving signal channel switch circuits controlled by the DSP chip to form an ultrasonic echo signal; the transmitting/receiving signal channel switch circuits controlled by the DSP chip receive the ultrasonic echo signal emitted from the four transducers and input the ultrasonic echo signal to the echo signal conditioning and collection circuit, the high speed ADC in the echo signal conditioning and collection circuit accomplishes data conversion.

9. A method to control an ultrasonic gas flow meter transmitter based on FPGA and DSP, consisting of a main monitoring program and various subroutine modules;

the main monitoring program is a master scheduling program, the various subroutine modules are an initialization module, a FRAM read-write module, a channel switch module, a communication module, a data transmission to FPGA module, a pulse output module, an interrupt service routine, a calculation module and a liquid crystal display module; the main monitoring program implements each function of the ultrasonic gas flow meter transmitter by calling each program module;

specific manipulation steps of the main monitoring program as follows:

(1) initialization of the circuit system after the circuit system is powered, the DSP chip accomplishing initialization of each section: including assigning GPIO ports of the DSP chip, cutting off initialization of an internal timer 1 of the DSP chip, initializing a liquid crystal display module, reading accumulated flow rates in the FRAM read-write module, initializing each parameter of a meter, and creating 4 queues, each of the queues consisting of 50 digital vacancies, the 4 queues configured to store propagation time of ultrasonic waves received by 4 transducers; whenever one new propagation time data enters, data on the front of each of the queues abandoned, the new propagation time data added on the end of the queue, in a subsequent measuring process, downstream and upstream average propagation time of a dual channel ultrasonic flow meter calculated in real time according to data of the four queues;

(2) circulation of flow detection the program entering circulation of flow detection after the circuit system is initiated; firstly the DSP chip switching transducer transmitting and receiving channels by changing output status of corresponding GPIO ports, order of switching channels: the first transducer transmitting while the third transducer receiving; the second transducer transmitting while the fourth transducer receiving; the third transducer transmitting while the first transducer receiving; the fourth transducer transmitting while the second transducer receiving; switching processes above cycled continuously; noticing the FPGA chip to start measuring after switching channels, the DSP chip required to wait for the FPGA chip to receive signals;

(3) waiting for the FPGA chip to control high speed DAC and high speed ADC to accomplish signal drive and echo signal collection the DSP chip sending a start-to-measure signal to the FPGA chip, the FPGA chip immediately enabling an internal delayed module, and waveform data stored in a ROM module in the FPGA chip called simultaneously to be transferred to the driving signal generation and amplification circuit; then output to the first transducer, or the second transducer, or the third transducer, or the fourth transducer with a direct injection dual channel structure through transmitting/receiving signal channel switch circuits controlled by the DSP chip, the first transducer, or the second transducer, or the third transducer, or the fourth transducer emitting ultrasonic waves;

the ultrasonic waves arriving at a corresponding receiving transducer after some propagation time; the third transducer, or the fourth transducer, or the first transducer, or the second transducer receiving the ultrasonic waves to form an echo signal; the transmitting/receiving signal channel switch circuits controlled by the DSP chip receiving the echo signal emitted from one transducer and inputting the echo signal to the echo signal conditioning and collection circuit; the high speed ADC in the echo signal conditioning and collection circuit accomplishing data conversion; RAM_2PORT module in the FPGA chip configured to temporarily store a conversion code value of the high speed ADC, when predefined time determined by a delayed circuit is up, pulling up a preset GPIO port of the DSP chip to inform completion of signal collection to the DSP chip;

(4) data duplication the DSP chip duplicating the data stored in the RAM_2PORT module in the FPGA chip to the RAM in the DSP chip after detecting a high level of a preset terminal, so as to provide the DSP chip to process by digital signals;

(5) the DSP chip processing the data, calculating propagation time of the ultrasonic waves the DSP chip processing the duplicated data, calculating propagation time T of each of the ultrasonic waves by:

$$T = 1/8 \sum_{i=1}^{8} \tau_i - t' \quad (4)$$

where $\tau_i$ (i=1, 2, 3 . . . 8) is zero-crossing time, t' is a stationary deviation value, the deviation value is obtained by calculating at zero flow;

(6) calculating an instantaneous flow rate obtaining one propagation time of the ultrasonic waves from a transducer to another transducer by one loop of steps (2)~(5);

switching different transmitting transducers and receiving transducers in step (2) to measure propagation time of each downstream and upstream propagating channel successively in sequence; after four loops as such, measurement of propagation time of downstream and upstream propagating dual channel accomplished, placing the four propagation time in the 4 queues created in the step (1) respectively;

processing five times of such measurement to calculate the average propagation time of downstream and upstream propagating dual channels, calculating an average flow as an instantaneous flow rate to display according to the average propagation time;

an equation of the instantaneous flow rate:

$$Q = \frac{\pi D^2}{4} \frac{L}{2\cos\theta} \frac{\Delta t}{t_s t_n} = k_f \frac{\Delta t}{t_s t_n} \quad (5)$$

where Q is a measured instantaneous flow rate, D is a diameter of a pipe, L is a length of the channel, $\theta$ is an angle of a channel angle, the channel angle is an angle between a propagation path of ultrasonic waves and a pipe axis; $t_s$, $t_n$ and $\Delta t$ respectively are forwardly flowing propagation time, backwardly flowing propagation time and a time difference of them, $k_f$ is a meter parameter;

obtaining a revised instantaneous flow rate after revising manipulation;

(7) calculating accumulated flow rates an interrupt service routine for the internal timer 1 of the DSP chip calculating accumulated flow rates after achieving the revised instantaneous flow rate to ensure accumulation once a second, which means the timer cutoff is generated by the DSP chip internal timer 1, a period is 1 second; a timer cutoff service program firstly reading a result of the instantaneous flow rate calculated by the main monitoring program and accumulating to achieve the accumulated flow rates; updating a parameter of the pulse output module according to a value of the instantaneous flow rate, outputting pulse with certain frequency to represent the measured instantaneous flow rate; subsequently, setting a time marker of the timer to be 1 to update liquid crystal display in the main monitoring program and processing host computer communication.

10. The method to control an ultrasonic gas flow meter transmitter based on FPGA and DSP according to claim 9, wherein on-chip logic and storage resources of the FGPA chip are equipped with 7 functional modules, respectively are a frequency division module, an ADC control module, an RAM_2PORT module, a DAC control module, a ROM module, a delay module and a SignalTap module; the frequency division module is configured to modulate 20 MHz clock signals input from outside to be 5 MHz sampling clock output to the high speed ADC; the ADC control module is configured to move the conversion code value of the high speed ADC to the RAM_2PORT module in the FPGA chip; the RAM_2PROT module is configured to store the high speed ADC conversion code value, when storage of the conversion code value of the high speed ADC achieves a certain amount, the DSP chip receives a ready-to-read signal, the stored high speed ADC conversion code value is transported to the DSP chip in accordance with a certain speed; the DAC control module is configured to move the waveform data stored in the ROM module to the high speed DAC to generate a corresponding excitation waveform; the delay module is configured to control the RAM_2PROT module to start storing the conversion code value of the high speed ADC undergoing predefined delayed time after excitation signals are sent for saving storage space; the Signal-Tap module is mainly configured to observe the conversion code value of the high speed ADC in real time after downloading programs for convenience of program modification and adjustment;

the DSP chip receives the high speed ADC conversion code value stored in the FPGA chip by a GPIO module; moreover, one GPIO of the DSP chip is connected to the FPGA chip as a data latch signal; the DSP chip enables the data latch signal after receiving the ready-to-read signal sent by FPGA and reads one conversion code value of the high speed ADC in the FPGA chip; simultaneously, an indicator in the FPGA chip shifts down 1 line, the manipulation above is repeated until all the data stored in the FPGA chip is read; after reading, the DSP chip sends a reset command to the FPGA chip to clear data in RAM_2PORT space and the delayed module in the FPGA chip and get ready for next measurement; moreover, the GPIO module of the DSP chip accomplishes keyboard input and liquid crystal display; a PWM module accomplishes pulse output of flow results to demarcate later gas flow rates; an SCI module accomplishes serial communication with the host computer to store and analyze flow results; an SPI module accomplishes a bidirectional read-write with the ferromagnetic random access memory FRAM, when the DSP chip detects power-off reset, the DSP chip writes accumulated flow rates and the meter parameters in FRAM.

11. The method to control an ultrasonic gas flow meter transmitter based on FPGA and DSP according to claim 9, wherein the plurality of program modules further comprise a watchdog module, the system selects an external watchdog to prevent the program from fleeting; moreover, the external watchdog further has functions of button reset, power-on/power-off reset and low voltage surveillance.

* * * * *